US007790910B2

(12) United States Patent
MacDonald et al.

(10) Patent No.: US 7,790,910 B2
(45) Date of Patent: Sep. 7, 2010

(54) PROCESS FOR THE PREPARATION OF 7α-ALKYLATED 19-NORSTEROIDS

(75) Inventors: Peter Lindsay MacDonald, Gentilino (CH); Ettore Bigatti, Balerna (CH); Pierluigi Rossetto, Balerna (CH)

(73) Assignee: Sicor Inc., Irvine, CA (US)

( * ) Notice: Subject to any disclaimer, the term of this patent is extended or adjusted under 35 U.S.C. 154(b) by 1427 days.

(21) Appl. No.: 11/192,071

(22) Filed: Jul. 27, 2005

(65) Prior Publication Data
US 2006/0030552 A1  Feb. 9, 2006

Related U.S. Application Data

(60) Provisional application No. 60/633,927, filed on Dec. 6, 2004, provisional application No. 60/600,292, filed on Aug. 9, 2004, provisional application No. 60/591,689, filed on Jul. 27, 2004.

(51) Int. Cl.
    *C07J 1/00* (2006.01)
(52) U.S. Cl. ...................................... 552/628
(58) Field of Classification Search ................. 552/628
    See application file for complete search history.

(56) References Cited

U.S. PATENT DOCUMENTS

| 4,659,516 | A | 4/1987 | Bowler et al. |
| 5,986,115 | A | 11/1999 | Bohlmann et al. |
| 6,288,051 | B1 | 9/2001 | Bittler et al. |
| 6,500,669 | B1 | 12/2002 | Essigmann et al. |
| 6,780,855 | B2 * | 8/2004 | Bohlmann et al. ......... 514/182 |

| 2003/0069434 | A1 | 4/2003 | Bohlmann et al. |
| 2005/0033085 | A1 | 2/2005 | Warren et al. |

FOREIGN PATENT DOCUMENTS

| DE | 24 29 040 | | 1/1975 |
| DE | 196 22 457 | | 11/1997 |
| EP | 0138504 | | 7/1988 |
| WO | WO 93/10741 | | 6/1993 |
| WO | WO 99/33855 | * | 7/1999 |
| WO | WO 99/42109 | | 8/1999 |
| WO | WO 02/32922 | | 4/2002 |
| WO | WO 03/031399 | | 4/2003 |
| WO | WO 03/045972 | | 6/2003 |
| WO | WO 98/07740 | | 7/2003 |

OTHER PUBLICATIONS

Bucourt, et al., "New Biospecific Adsorbents For The Purification Of Estradiol Receptor", *Journal of Biological Chemistry*, 1978, pp. 8221-8228, vol. 253, No. 22.
Dasilva, et al., "Synthesis And Structure-Affinity Of A Series of 7'alpha!-Undecylestradiol Derivatives: A Potential Vector For Therapy And Imaging Of Estrogen-Receptor-Positive Cancers", *Journal of Medicinal Chemistry*, 1990, pp. 430-434, vol. 33, No. 1.
Skaddan, et al., "Synthesis And Binding Affinities Of Novel Re-Containing 7.Alpha.-Substituted Estradiol Complexes: Models For Breast Cancer Imaging Agents", *Journal of Organic Chemistry*, 1999, pp. 8108-8121, vol. 64, No. 22.
Bowler, et al., *Steroids*, 1989, vol. 54, 71-99.
Rao, et al., *Steroids*, 1994, vol. 59, 621-627.

* cited by examiner

*Primary Examiner*—Barbara P Badio
(74) *Attorney, Agent, or Firm*—Kenyon & Kenyon LLP

(57) ABSTRACT

Processes useful in the preparation of pharmaceutical compounds such as fulvestrant and processes for the preparation of fulvestrant.

5 Claims, 13 Drawing Sheets nandrolone acetate, 6 dehydro
Cp 9294

Cp 9339

Cp 9340

PROCESS FOR THE PREPARATION OF 7α-ALKYLATED 19-NORSTEROIDS

CROSS REFERENCE TO RELATED APPLICATIONS

This application claims the benefit of U.S. provisional application Ser. Nos. 60/591,689, filed Jul. 27, 2004; 60/600,292, filed Aug. 9, 2004; and 60/633,927, filed Dec. 6, 2004, the contents of which are incorporated herein in their entirety

FIELD OF THE INVENTION

The invention relates to a new processes useful in the preparation of pharmaceutical compounds such as fulvestrant.

BACKGROUND

There is a growing recognition of the need for effective therapeutic strategies to treat breast cancer patients that are less toxic than chemotherapy. Since the discovery of the hormonal dependency of many breast cancers, endocrine therapy has been extensively investigated.

Fulvestrant is a pure antiestrogen that represent a significant breakthrough in the treatment of breast cancer. Despite its pure antagonist activity, studies on ovariectomized rats have confirmed that fulvestrant, in contrast to Tamoxifen which acts like estrogen to reduce periosteal bone formation, does not alter estrogen-like or antiestrogenic effects. Fulvestrant also has some distinct advantages on target organs other than breast tissue.

Fulvestrant is a steroidal pure antiestrogen with a chemical structure similar to estradiol. Studies of estrogen receptor (ER) function have demonstrated that estradiol binding to the ER initiate a sequence of events. Fulvestrant antagonizes estrogen action by occupying the ER and preventing estrogen-stimulated gene activation, thus interfering with the estrogen related processes essential for cell-cycle completion.

Fulvestrant, 7-alpha-[9-(4,4,5,5,5pentafluoropentylsulphinyl)nonyl]-estra-1,3,5(10)-triene-3,17β-diol, has the following formula:

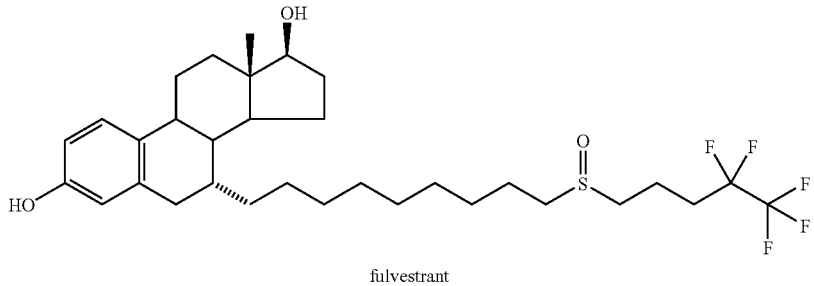

fulvestrant

WO Patent application No. 02/32922 describes a process for preparing an intermediate compound useful for preparing, e.g. fulvestrant, which process comprises aromatization of a compound, and thereafter if necessary or desired, carrying out one or more of the following steps: (i) removing any hydroxy protecting group; (ii) converting a precursor group to a different such group.

EP Patent No. 0138504 relates to certain 7α-substituted derivatives of oestradiol and related steroids which possess antioestrogenic activity. U.S. Pat. No. 4,659,516, EP Patent No. 0138504 and Bowler, Steroids 1989, 54, 71 describe a process for making steroids such as fulvestrant, by which 1,6-conjugate addition of an alkyl group to an estra-4,6-diene-3-one gave a ratio of 7α- to 7β-epimer of 1.2:1 (isolated). In WO 02/92322 it is stated that the ratio of epimers obtained using this process on an industrial scale is 1.9:1.

U.S. Pat. No. 6,288,051 describes 7α-(5-methylaminopentyl)-estratrienes.

There remains a need in the art for improved methods of preparing fulvestrant and other 7α-alkylated 19-norsteroids.

SUMMARY OF THE INVENTION

The invention relates to A compound of formula (I):

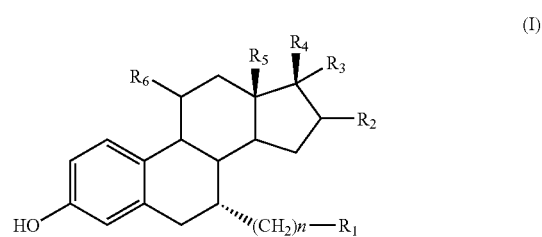

wherein
n is an integer ranging from 3 to 14,
$R_1$ is selected from the group consisting of Br, Cl, I, free base or a salt form of isothiouronium, or SH;
$R_2$ is either hydrogen, $C_{1-6}$ alkyl, hydroxyl, protected hydroxy, or halo;
$R_3$ is either hydrogen, $C_{1-6}$ alkyl, $C_{2-6}$ alkenyl, or $C_{2-6}$ alkynyl;
$R_4$ is either hydroxy, or a $C_{1-6}$ acyloxy;
$R_5$ is $C_{1-6}$ alkyl; and
$R_6$ is either hydrogen, $C_{1-6}$ alkyl, hydroxyl, protected hydroxy, or halo.

In one embodiment, n is 9, $R_1$ is Br, $R_2$, $R_3$, and $R_6$ are hydrogens, $R_4$ is hydroxy and $R_5$ is methyl.

In one embodiment, n is 9, $R_1$ is Br, $R_2$, $R_3$, and $R_6$ are hydrogens, $R_4$ is acetyloxy and $R_5$ is methyl.

In one embodiment, n is 9, $R_1$ is a hydrobromide salt of isothiouronium, $R_2$, $R_3$, and $R_6$ are hydrogens, $R_4$ is acetyloxy and $R_5$ is methyl.

In one embodiment, n is 9, $R_1$ is a hydrobromide salt of isothiouronium, $R_2$, $R_3$, and $R_6$ are hydrogens, $R_4$ is hydroxy and $R_5$ is methyl.

In one embodiment, n is 9, $R_1$ is SH, $R_2$, $R_3$, and $R_6$ are hydrogens, $R_4$ is acetyloxy and $R_5$ is methyl.

In one embodiment, n is 9, $R_1$ is SH, $R_2$, $R_3$, and $R_6$ are hydrogens, $R_4$ is hydroxy and $R_5$ is methyl.

The invention also relates to a compound of formula

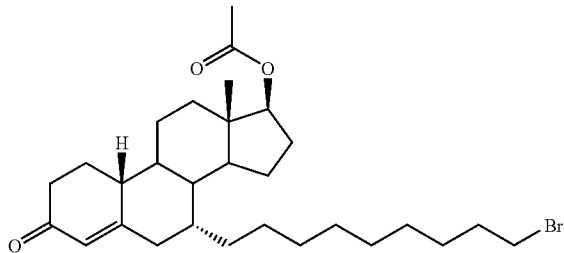

The invention also relates to a process for preparing the compound of formula (II),

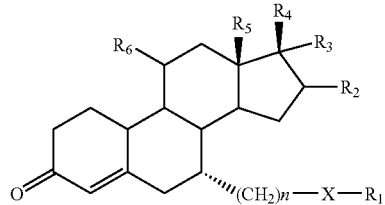

(II)

comprising:

a) combining a 19-nor-androsta-4,6-diene-3-one of formula (III)

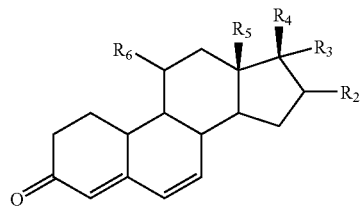

b) (III)

with an etheral solvent, to obtain a solution;

b) cooling the solution to a temperature of about −60° C. to about 30° C.;

c) adding to the solution of step b), in a drop-wise manner, a solution of the compound of formula (IV)

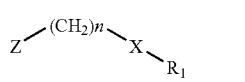

(IV)

in an etheral solvent to obtain a reaction mixture;

d) quenching the reaction mixture; and e) recovering the compound of formula (II);

wherein n is an integer ranging from 3 to 14,

X is either O or S;

$R_1$ is a $C_{1-10}$ haloalkyl or a hydroxy protecting group;

$R_2$ is either hydrogen, $C_{1-6}$ alkyl, hydroxyl, protected hydroxy, or halo;

$R_3$ is either hydrogen, $C_{1-6}$ alkyl, $C_{2-6}$ alkenyl, or $C_{2-6}$ alkynyl;

$R_4$ is a $C_{1-6}$ acyloxy;

$R_5$ is $C_{1-6}$ alkyl; and $R_6$ is either hydrogen, $C_{1-6}$ alkyl, hydroxyl, protected hydroxy, or halo; and z is a metal halide of the formula $R_7M$, wherein M is a metal atom; and $R_7$ is a halogen atom.

In one embodiment of the process, n is 9, X is O, $R_1$ is tertbutyl-dimethylsilyl (TBDMS), $R_2$, $R_3$ and $R_6$ are hydrogens, $R_4$ is acetyloxy and $R_5$ is methyl.

In one embodiment of the process, n is 5, X is O, $R_1$ is TBDMS, $R_3$ and $R_6$ are hydrogens, $R_4$ is acetyloxy and $R_5$ is methyl.

In one embodiment of the process, n is 9, X is S, $R_1$ is —$(CH_2)_3CF_2CF_3$, $R_2$, $R_3$ and $R_6$ are hydrogens, $R_4$ is acetyloxy and $R_5$ is methyl.

In one embodiment of the process, M is a metal atom selected from the group consisting of magnesium, zinc, aluminum, copper, copper-lithium and titanium.

In one embodiment of the process, M is magnesium.

In one embodiment of the process, $R_7$ is selected from the group consisting of Cl, Br and I.

In one embodiment of the process, $R_7$ is Br.

In one embodiment of the process, a copper catalyst is a combined in step a) with the 19-nor-androsta-4,6-diene-3-one of formula (III) and the etheral solvent.

In one embodiment of the process, said copper catalyst is in the form of Cu(I)Y, wherein Y is Cl, Br or I.

In one embodiment of the process, said copper catalyst is Cu(I)Cl.

In one embodiment of the process, the compound of formula (II) obtained in step e) has a ratio of 7α- to 7β-epimer of about 2.5:1 to about 12.1:1.

In one embodiment of the process, the compound of formula (II) obtained in step e) has a ratio of 7α- to 7β-epimer of about 12.1:1.

In one embodiment of the process, the etheral solvent in step a) is selected from the group consisting of: diethyl ether, THF and glyme.

In one embodiment of the process, said etheral solvent is THF.

In one embodiment of the process, the solution of step b) is cooled to a temperature of about −20° C. to about −10° C.

In one embodiment of the process, the reaction mixture in step d) is quenched by one of the reagents selected from the group consisting of: $NH_4Cl$, HCl, water, acetic acid and a mixture of $NH_4Cl$ with $NH_4OH$.

In one embodiment of the process, the reaction mixture is quenched with acetic acid.

In one embodiment of the process, the process further comprises converting the compound of formula (II) obtained in step e) to fulvestrant.

The invention further relates to a process for preparing the compound of formula (V), (V)

comprising combining a compound of formula (II)

(II)

with acetonitrile and triphenylphosphine dibromide for a sufficient amount of time for conversion into the compound of formula (V);
wherein
n is an integer ranging from 3 to 14,
X is O;
$R_1$ is a hydroxy protecting group;
$R_2$ is either hydrogen, $C_{1-6}$ alkyl, hydroxyl, protected hydroxy, or halo;
$R_3$ is either hydrogen, $C_{1-6}$ alkyl, $C_{2-6}$ alkenyl, or $C_{2-6}$ alkynyl;
$R_4$ is a $C_{1-6}$ acyloxy;
$R_5$ is $C_{1-6}$ alkyl; and
$R_6$ is either hydrogen, $C_{1-6}$ alkyl, hydroxyl, protected hydroxy, or halo.

In one embodiment of the process, n is 9, $R_1$ is tertbutyldimethylsilyl (TBDMS), $R_2$, $R_3$ and $R_6$ are hydrogens, $R_4$ is acetyloxy and $R_5$ is methyl.

In one embodiment of the process, the compound of formula (II) is combined with the acetonitrile and triphenylphosphine dibromide at a temperature of about 10° C. to about 12° C.

In one embodiment of the process, the process further comprises converting the obtained product to fulvestrant.

The invention further relates to a process for preparing the compound of formula (VI)

(VI)

wherein $R_4$ is hydroxy, comprising combining the compound of formula (VI), wherein $R_4$ is a $C_{1-6}$ acyloxy, with a $C_{1-6}$ alcohol and mineral acid, at a temperature of about 50° C. to about 70° C.;
wherein
n is an integer ranging from 3 to 14,
$R_2$ is either hydrogen, $C_{1-6}$ alkyl, hydroxyl, protected hydroxy, or halo;
$R_3$ is either hydrogen, $C_{1-6}$ alkyl, $C_{2-6}$ alkenyl, or $C_{2-6}$ alkynyl;
$R_5$ is $C_{1-6}$ alkyl; and
$R_6$ is either hydrogen, $C_{1-6}$ alkyl, hydroxyl, protected hydroxy, or halo.

In one embodiment of the process, $R_2$, $R_3$ and $R_6$ are hydrogens, and $R_5$ is methyl.

In one embodiment of the process, the mineral acid is HBr.

In one embodiment of the process, the temperature is about 60° C.

In one embodiment of the process, the process further comprises converting the obtained product to fulvestrant.

The invention further relates to a process for preparing the compound of the formula (I)

(I)

comprising combining the compound of formula (VI)

(VI)

with a solvent selected from a $C_{1-6}$ aromatic hydrocarbon, a straight or branched $C_{1-4}$ alcohol, a $C_{1-4}$ alkyl amide and mixtures thereof and thiourea; and recovering the compound of formula (I)
wherein
n is an integer ranging from 3 to 14,
$R_1$ is a free base or a salt form of isothiouronium;
$R_2$ is either hydrogen, $C_{1-6}$ alkyl, hydroxyl, protected hydroxy, or halo;
$R_3$ is either hydrogen, $C_{1-6}$ alkyl, $C_{2-6}$ alkenyl, or $C_{2-6}$ alkynyl;
$R_4$ is either hydroxy or $C_{1-6}$ acyloxy;
$R_5$ is $C_{1-6}$ alkyl; and
$R_6$ is either hydrogen, $C_{1-6}$ alkyl, hydroxyl, protected hydroxy, or halo.

In one embodiment of the process, n is 9, $R_1$ is a hydrobromide salt of isothiouronium, $R_2$, $R_3$ and $R_6$ are hydrogens, $R_4$ is acetyloxy and $R_5$ is methyl.

In one embodiment of the process, n is 9, $R_1$ is a hydrobromide salt of isothiouronium, $R_2$, $R_3$ and $R_6$ are hydrogens, $R_4$ is hydroxy and $R_5$ is methyl.

In one embodiment of the process, the solvent is selected from the group consisting of toluene, xylene, benzene, methanol, ethanol, propanol, isopropanol, butanol, dimethylacetamide and mixtures thereof.

In one embodiment of the process, the solvent is a mixture of toluene and isopropanol or dimethylacetamide.

In one embodiment of the process, the process further comprises converting the obtained product to fulvestrant.

The invention further relates to a process for preparing the compound of the formula (VII)

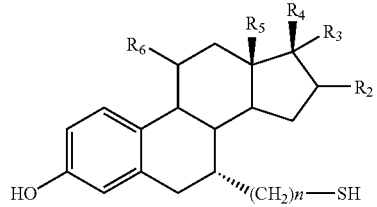

(VII)

comprising combining compound of the formula (I)

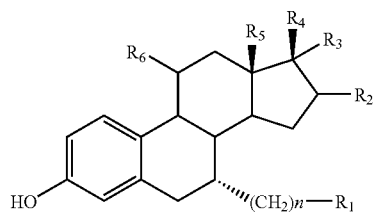

(I)

with a base in the presence of an apolar protic organic solvent at ambient temperature;

wherein
   n is an integer ranging from 3 to 14,
   $R_1$ is a free base or a salt form of isothiouronium;
   $R_2$ is either hydrogen, $C_{1-6}$ alkyl, hydroxyl, protected hydroxy, or halo;
   $R_3$ is either hydrogen, $C_{1-6}$ alkyl, $C_{2-6}$ alkenyl, or $C_{2-6}$ alkynyl;
   $R_4$ is either hydroxy or $C_{1-6}$ acyloxy;
   $R_5$ is $C_{1-6}$ alkyl; and
   $R_6$ is either hydrogen, $C_{1-6}$ alkyl, hydroxyl, protected hydroxy, or halo.

In one embodiment of the process, n is 9, $R_1$ is a hydrobromide salt of isothiouronium, $R_2$, $R_3$ and $R_6$ are hydrogens, $R_4$ is acetyloxy and $R_5$ is methyl.

In one embodiment of the process, n is 9, $R_1$ is a hydrobromide salt of isothiouronium, $R_2$, $R_3$ and $R_6$ are hydrogens, $R_4$ is hydroxy and $R_5$ is methyl.

In one embodiment of the process, the base is an alkali metal base.

In one embodiment of the process, the base is NaOH.

In one embodiment of the process, the aprotic polar organic solvent is dimethylacetamide or acetonitrile.

In one embodiment of the process, said aprotic polar organic solvent is dimethylacetamide.

In one embodiment of the process, the process further comprises converting the obtained product to fulvestrant.

The invention further relates to a process for preparing the compound of the formula (I)

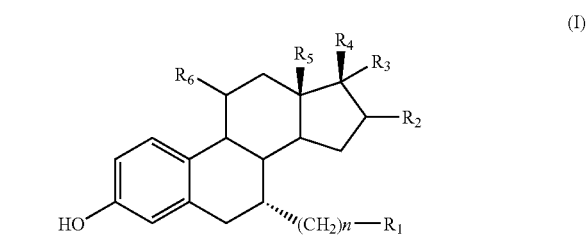

(I)

comprising combining the compound of formula (VII)

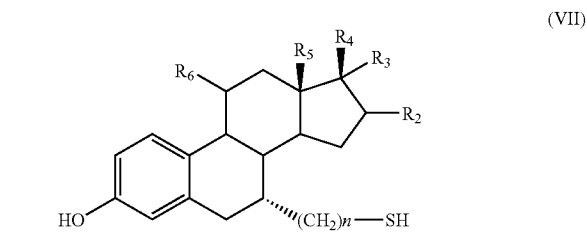

(VII)

with 4,4,5,5,5-pentafluoropentane-1-ol mesylate at an ambient temperature;

combining the obtained reaction mixture with a base in the presence of an organic solvent; and recovering the compound of the formula (I);

wherein
   n is an integer ranging from 3 to 14,
   $R_1$ is —S—$(CH_2)_3CF_2CF_3$
   $R_2$ is either hydrogen, $C_{1-6}$ alkyl, hydroxyl, protected hydroxy, or halo;
   $R_3$ is either hydrogen, $C_{1-6}$ alkyl, $C_{2-6}$ alkenyl, or $C_{2-6}$ alkynyl;
   $R_4$ is either hydroxy or $C_{1-6}$ acyloxy;
   $R_5$ is $C_{1-6}$ alkyl; and
   $R_6$ is either hydrogen, $C_{1-6}$ alkyl, hydroxyl, protected hydroxy, or halo.

In one embodiment of the process, n is 9, $R_2$, $R_3$ and $R_6$ are hydrogens, $R_4$ is a acetyloxy and $R_5$ is methyl.

In one embodiment of the process, n is 9, $R_2$, $R_3$ and $R_6$ are hydrogens, $R_4$ is acetyloxy and $R_5$ is methyl.

In one embodiment of the process, the base is an alkali metal base.

In one embodiment of the process, the base is KOH.

In one embodiment of the process, the organic solvent is a $C_{1-6}$ alcohol.

In one embodiment of the process, the organic solvent is methanol.

In one embodiment of the process, wherein the process further comprises converting the obtained product to fulvestrant.

The invention further relates to a process for preparing fulvestrant comprising:

a) combining compound of formula 9294

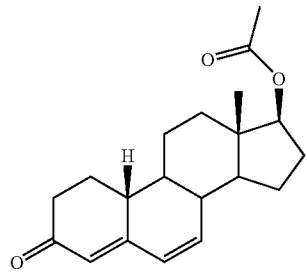

9294 with an etheral solvent, to obtain a solution;

b) adding to the solution of step a), in a drop-wise manner, a solution of the compound of formula 9318

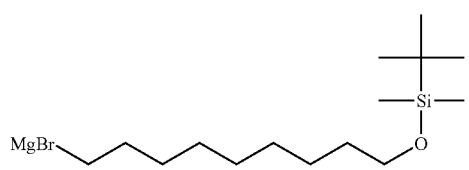

9318 in an etheral solvent to obtain a first reaction mixture comprising a compound of formula 9295;

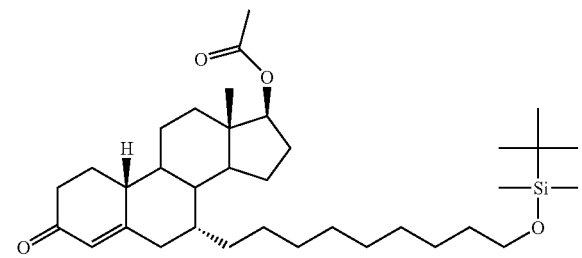

9295 c) quenching the first reaction mixture;
d) recovering compound 9295;
e) combining compound 9295 with acetonitrile and triphenylphosphine dibromide for a time sufficient to convert compound 9295 into a compound of formula 9341

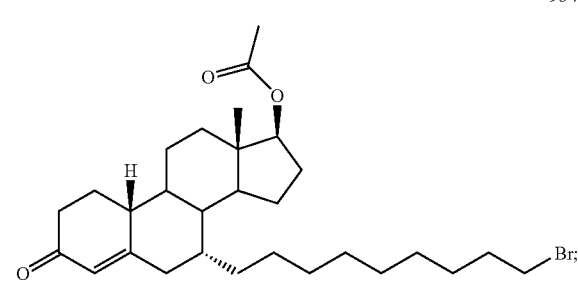

9341 f) aromatizing the A ring of compound 9341 by reacting compound 9341 with a mixture of lithium bromide and copper bromide in acetonitrile to obtain a compound of formula 9342

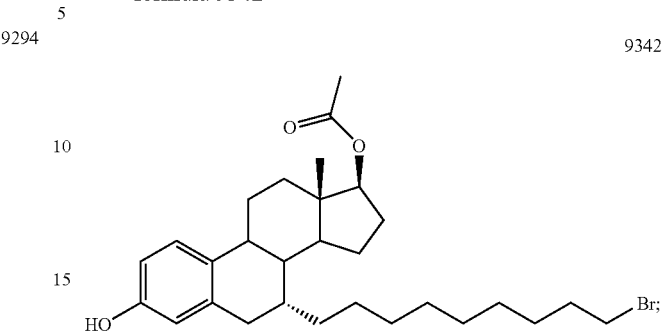

9342 g) combining compound 9342 with $C_{1-4}$ alcohol and a mineral acid, at a temperature of about 50° C. to about 70° C. to obtain a compound of formula 9354

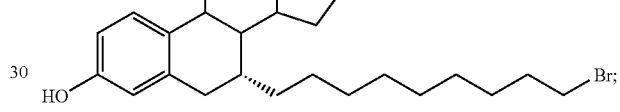

9354 h) combining compound 9354 with a solvent selected from a $C_{1-6}$ aromatic hydrocarbon, a straight or branched $C_{1-4}$ alkyl amide and mixtures thereof and thiourea to provide a compound of formula 9388

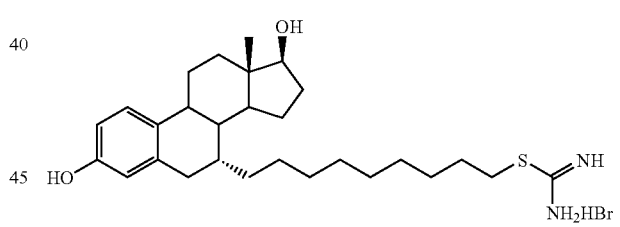

9388 and recovering compound 9388;

i) combining compound 9388 with a base at ambient temperature to obtain a compound of formula 9389

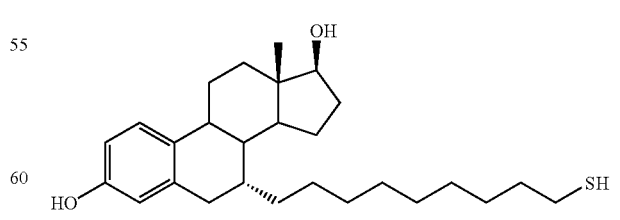

9389 j) combining compound 9389 with 4,4,5,5,5-pentafluoropenatane-1-ol mesylate at an ambient temperature to provide a second reaction mixture and then combining the second reaction mixture with a base to obtain a compound of formula 9304

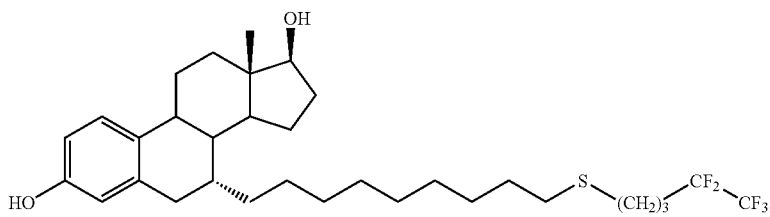

9304 and k) combining compound 9304 and a mixture of a $C_{1-4}$ alcohol and an etheral solvent with an aqueous solution of an oxidizing agent at a temperature of about 5° C. for about 12 hours to provide fulvestrant.

The invention further relates to a process for preparing fulvestrant comprising:

a) combining compound of formula 9294

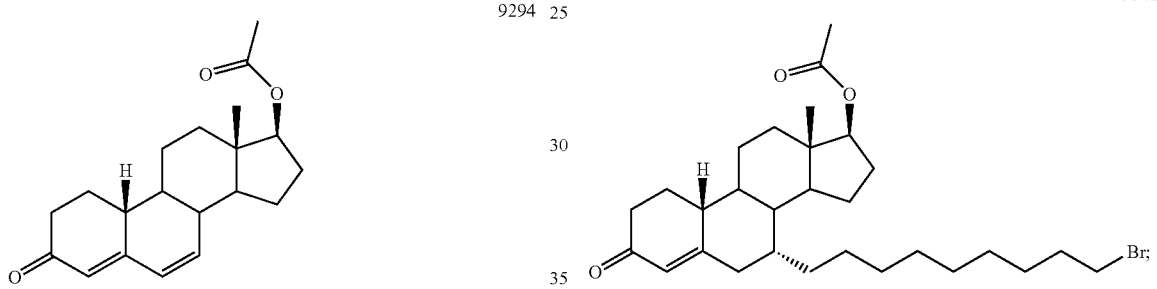

with an etheral solvent, to obtain a solution;

b) adding to the solution of step a), in a drop-wise manner, a solution of the compound of formula 9318

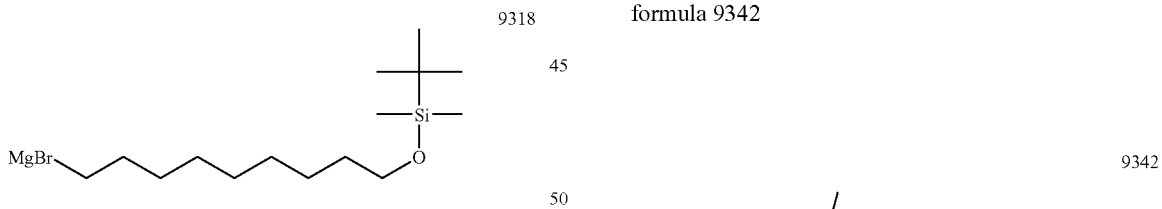

in an etheral solvent to obtain a first reaction mixture comprising a compound of formula 9295;

c) quenching the first reaction mixture;

d) recovering compound 9295;

e) combining compound 9295 with acetonitrile and triphenylphosphine dibromide for a time sufficient to convert compound 9295 into a compound of formula 9341

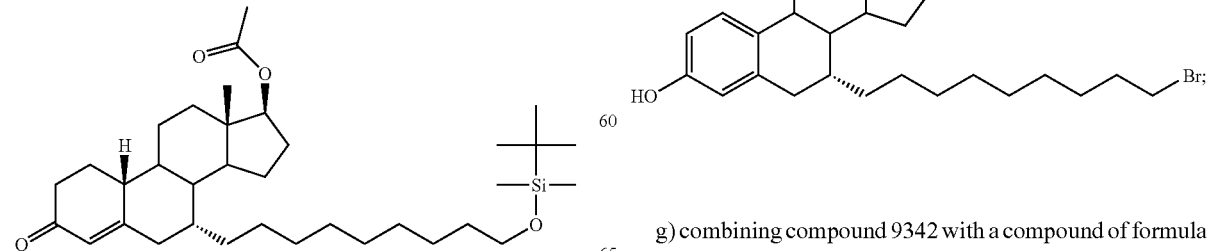

f) aromatizing the A ring of compound 9341 by reacting compound 9341 with a mixture of lithium bromide and copper bromide in acetonitrile to obtain a compound of formula 9342

9342 g) combining compound 9342 with a compound of formula 9383

HS(CH$_2$)$_3$CF$_2$CF$_3$    9383;

to provide a compound of formula 9363

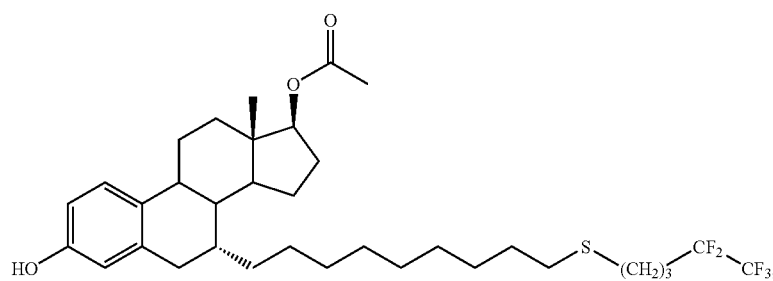

h) combining at ambient temperature, compound 9363 and a $C_{1-4}$ alcohol with an alkali base to obtain compound 9304

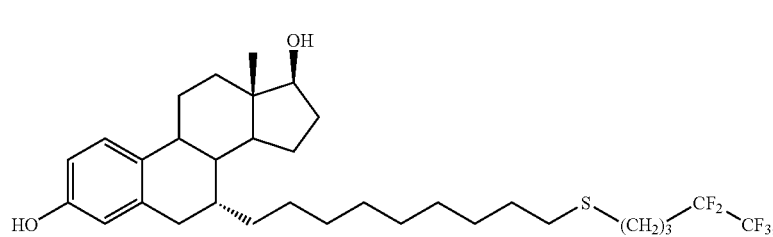

and i) combining compound 9304 and a mixture of a $C_{1-4}$ alcohol and an etheral solvent with an aqueous solution of an oxidizing agent at a temperature of about 5° C. for about 12 hours to provide fulvestrant.

The invention further relates to a process for preparing fulvestrant comprising a) combining compound of formula 9294

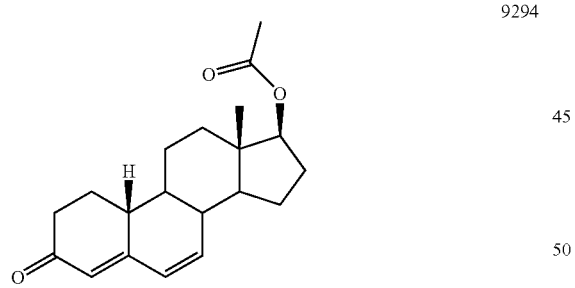

with an etheral solvent, to obtain a solution;

b) adding to the solution of step a), in a drop-wise manner, a solution of the compound of formula 9318

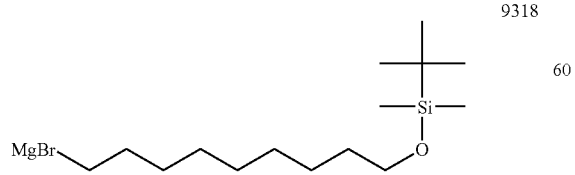

in an etheral solvent to obtain a first reaction mixture comprising a compound of formula 9295;

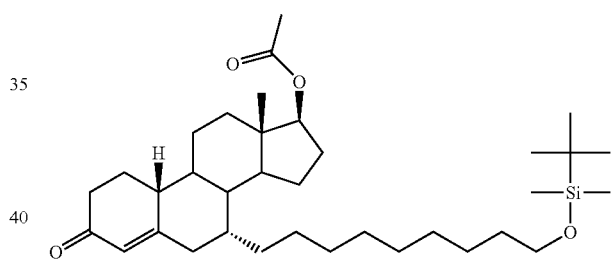

c) quenching the first reaction mixture;
d) recovering compound 9295;
e) combining compound 9295 with acetonitrile and triphenylphosphine dibromide for a time sufficient to convert compound 9295 into a compound of formula 9341

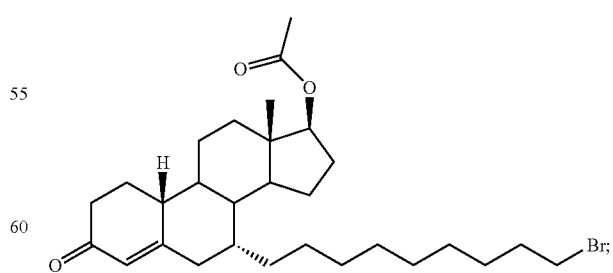

f) aromatizing the A ring of compound 9341 by reacting compound 9341 with a mixture of lithium bromide and copper bromide in acetonitrile to obtain a compound of formula 9342

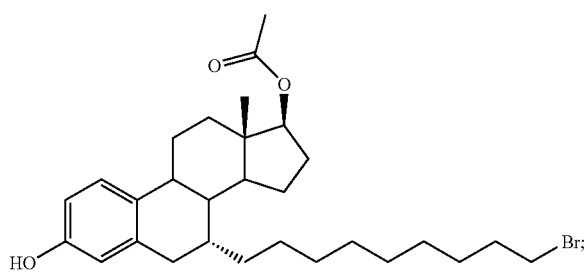

9342 g) combining compound 9342 with a solvent selected from a $C_{1-6}$ aromatic hydrocarbon, a straight or branched $C_{1-4}$ alkyl amide and mixtures thereof and thiourea to provide a compound of formula 9361

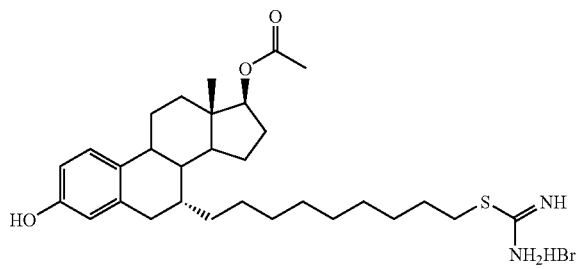

9361 and recovering compound 9361.

h) combining compound 9361 with a base at an ambient temperature to obtain a compound of formula 9362

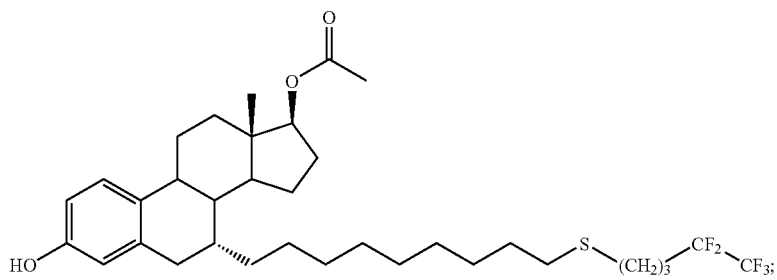

9362 i) combining compound 9362 with 4,4,5,5,5-pentafluoro-penatane-1-ol mesylate at ambient temperature to provide a second reaction mixture followed by combining the second reaction mixture with a base to obtain a compound of formula 9363

9363

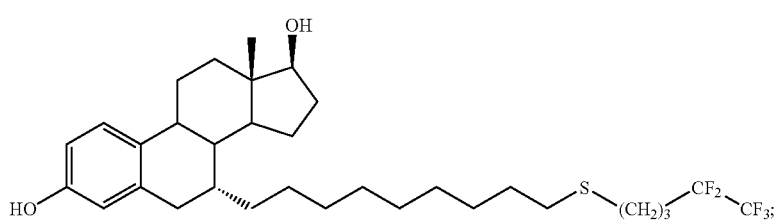

j) combining at ambient temperature compound 9363 and a $C_{1-4}$ alcohol with an alkali base to obtain a compound of formula 9304

9304 and k) combining compound 9304 and a mixture of a $C_{1-4}$ alcohol and an etheral solvent with an aqueous solution of an oxidizing agent at a temperature of about 5° C. for about 12 hours to provide fulvestrant.

The invention further relates to a process for preparing fulvestrant comprising a) reacting a compound of formula 9363

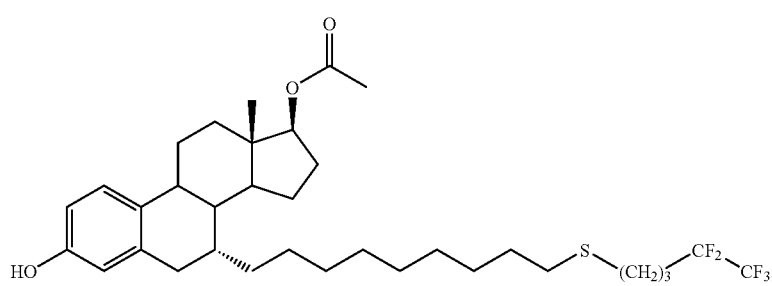

9363 with a mixture of a $C_{1-4}$ alcohol and an etheral solvent with an aqueous solution of an oxidizing agent at a temperature of about 5° C. for about 12 hours to provide a compound of formula 9368

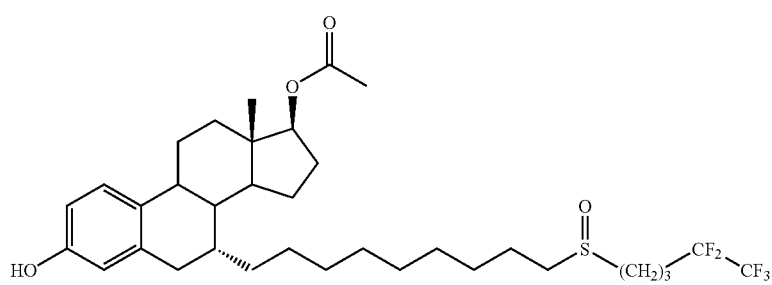

9368 and b) combining at ambient temperature compound 9368 and a $C_{1-4}$ alcohol with an alkali base to obtain fulvestrant.

DETAILED DESCRIPTION OF THE INVENTION

Figure 1:
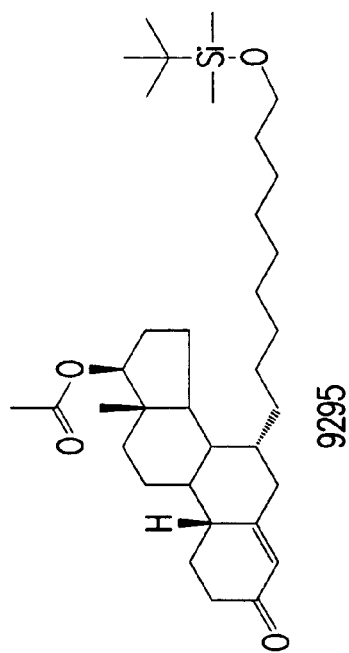
FIG. 1 is a schematic showing a method for making an intermediate, useful in the preparation of fulvestrant, according to the method of the invention.
Figure 1:
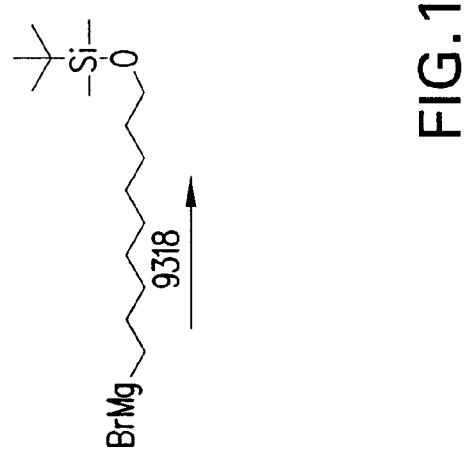
Figure 1:
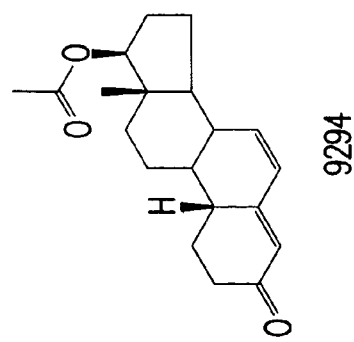

The phrase "precursor group," as used herein, means a functional group that can be readily converted to another functional group. Accordingly, the phrase "a group $R_4$ or a precursor group thereof" means a group $R_4$ or a group that can be readily converted to $R_4$. As a representative example, esters are a precursor group for an alcohol because the ester can be readily hydrolyzed to provide the alcohol.

The phrase "hydroxy protecting group" or "protected hydroxy," as used herein means a group that can replace the hydrogen of a hydroxyl, i.e., the hydrogen of an —OH group, and then be subsequently removed and replaced by a hydrogen to reform the hydroxyl group. The hydroxyl protecting group prevents the hydroxyl from reacting under a given set of conditions, which typically are necessary to per-form a reaction at another part of a molecule. After reaction at the other part of the molecule, the hydroxyl protecting group can be removed to provide the hydroxyl group. A list of suitable hydroxy protecting groups can be found in Protective Groups in Organic Synthesis, Third Edition, John Wiley, New York 1999. Representative hydroxyl protecting groups include, but are not limited to: alkyl or aryl ethers, silyl ethers and esters.

Representative hydroxyl protecting groups include, but are not limited to:

methyl ethers including, but not limited to, methoxymethyl; methylthiomethyl; t-butylthiomethyl; (phenyldimethyldiyl)methoxy-methyl; benzyloxymethyl; p-methoxybenzyl-oxymethyl; (4-methoxyphenoxy)methyl; guaiacolmethyl; t-butoxymethyl; 4-pentenyloxymethyl; siloxymethyl; 2-methoxyethoxymethyl; 2,2,2-trichloroethoxymethyl; bis(2-chloroethoxy)methyl; 2-(trimethylsilyl) ethoxymethyl; tetrahydropyran-2-yl; 3-bromotetrahydropyran-2-yl; 1-methoxycyclohexyl; 4-methoxytetrahydropyran-2-yl; 4-methoxytetrahydrothiopyran-2-yl; 4-methoxytetrahydrothiopyran-2-yl-S,S-dioxido; 1-[(2-chloro-4-methyl)phenyl]-4-methoxypiperidin-4-yl; 1,4-dioxan-2-yl; tetrahydrofuranyl; tetrahydrothiofuranyl; and 2,3, 3a,4,5,6,7,7a-octahydro-7,8,8-trimethyl-4,7-methanobenzofuran-2-yl;

ethyl ethers including, but not limited to, 1-ethoxyethyl; 1-(2-chloroethoxy)ethyl; 1-methyl-1-methoxyethyl; 1-methyl-i-benzyloxy-2-fluoroethyl; 2,2,2-trichloroethyl; 2-trimethylsilylethyl; 2-(phenylselenyl)ethyl; t-butyl; allyl; p-chlorophenyl; p-methoxyphenyl; and 2,4-dinitrophenyl, benzyl ethers including, but not limited to, benzyl; p-methoxybenzyl; 3,4-dimethoxybenzyl; o-nitrobenzyl; p-nitrobenzyl; p-halobenzyl; 2,6-dichlorobenzyl; p-cyanobenzyl; p-phenylbenzyl; 2- and 4-picolyl; 3-methyl-2-picolyl-N-oxide; diphenylmethyl; p,p'-dinitrobenzhydryl; 5-dibenzosuberyl; triphenylmethyl; a-naphthyldiphenylmethyl; p-methoxyphenyldiphenylmethyl; di(p-methoxyphenyl) phenylmethyl; tri(p-methoxyphenyl)methyl; 4-(4'-bromophenacyloxy)phenyldiphenylmethyl; 4,4'1,4"-tris(4,5-dichlorophthalimidophenyl)methyl; 4,4',4"-tris-(levulinoyloxyphenyl)methyl; 4,4',4"-tris (benzoyloxyphenyl)methyl; 3-(imidazol-1-ylmethyl)bis(4', 4"-dimethoxyphenyl)-methyl; 1,1-bis(4-methoxyphenyl)-1'-pyrenylmethyl; 9-anthryl; 9-(9-phenyl)xanthenyl; 9-(9-phenyl-10-oxo)anthryl; 1,3-benzodithiolan-2-yl; and benzisothiazolyl S,S-dioxido;

silyl ethers including, but not limited to, trimethylsilyl; triethylsilyl; triisopropylsilyl; dimethylisopropylsilyl; diethylisopropylsilyl; dimethylthexylsilyl; t-butyldimethylsilyl; t-butyl-diphenylsilyl; tribenzylsilyl; tri-p-xylylsilyl; triphenylsilyl; diphenylmethylsilyl; and t-butylmethoxyphenylsilyl;

esters including, but not limited to, formate; benzoylformate; acetate; chloroacetate; trichloroacetate; methoxyacetate; triphenylmethoxyacetate; phenoxyacetate; p-chlorophenoxyacetate; p-(phosphate)phenylacetate; 3-phenylproprionate; 4-oxopentanoate (levulinate); 4,4-(ethylenedithio)pentanoate; pivaloate; adamantoate; crotonate; 4-methoxycrotonate; benzoate; p-phenylbenzoate; and 2,4,6-trimethylbenzoate;

carbonates including, but not limited to, methyl carbonate; 9-fluorenyl-methylcarbonate; ethyl carbonate; 2,2,2-trichloroethyl carbonate; 2-(trimethylsilyl)ethyl carbonate; 2-(phenylsulfonyl)ethyl carbonate; 2-(triphenylphosphono)ethyl carbonate; isobutyl carbonate; vinyl carbonate; allyl carbonate; p-nitrophenyl carbonate; benzyl carbonate; p-methoxybenzyl carbonate; 3,4-dimethoxybenzyl carbonate; o-nitrobenzyl carbonate; p-nitrobenzyl carbonate; S-benzyl thiocarbonate; 4-ethoxy-1-naphthyl carbonate; and methyl dithiocarbonate;

protecting groups with assisted cleavage including, but not limited to, 2-iodobenzoate; 4-azidobutyrate; 4-nitro-4-methylpentanoate; o-(dibromomethyl)benzoate; 2-formylbenzenesulfonate; 2-(methylthiomethoxy)ethyl carbonate; 4-(methylthiomethoxy)-butyrate; and 2-(methylthiomethoxymethyl) benzoate;

miscellaneous esters including, but not limited to, 2,6-dichloro-4-methylphenoxyacetate; 2,6-dichloro-4-(1,1,3,3-tetramethyl-butyl)phenoxyacetate; 2,4-bis(1,1-dimethylpropyl)-phenoxy-acetate; chlorodiphenylacetate; isobutyrate; monosuccinoate; (E)-2-methyl-2-butenoate (tigloate); o-(methoxycarbonyl)benzoate; p-benzoate; a-naphthoate; nitrate; alkyl N,N,N',N'-tetramethylphosphorodiamidate; N-phenylcarbamate; borate; dimethylphosphinothioyl; and 2,4-dinitrophenyl-sulfenate;

sulfonates including, but not limited to, methanesulfonate (mesylate); benzylsulfonate; and tosylate; and silyl derivatives including, but not limited to, di-t-butylsilylene group; 1,3-(1,1,3,3-tetraisopropyldisiloxanylidene) derivative; tetra-t-butoxydisiloxane-1,3-diylidene derivative; cyclic carbonates; cyclic boronates; ethyl boronate; and phenyl boronate.

A preferred hydroxy protecting groups is $SiR_8R_9R_{10}$, wherein $R_8$, $R_9$, and $R_{10}$ are alkyl or branched alkyl containing 1 to 6 carbon atoms. Most preferably, $R_8$ and $R_9$ are methyl and $R_{10}$ is t-butyl.

Throughout this specification the rings of the compounds of the invention are designated using the lettering conventionally used for designating the rings of a steroid as depicted below:

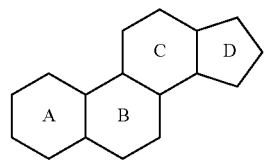

Accordingly, the A ring of a steroid is the most left ring of the compound of formula as drawn above.

The term "aromatizing," as used herein, means changing a ring structure that is not aromatic, i.e., either unsaturated or partially saturated, to a ring systems that is aromatic, i.e., a ring system that has a cyclic cloud of 4n+2 delocalized Π electrons.

One aspect of the present invention is a compound of formula (I):

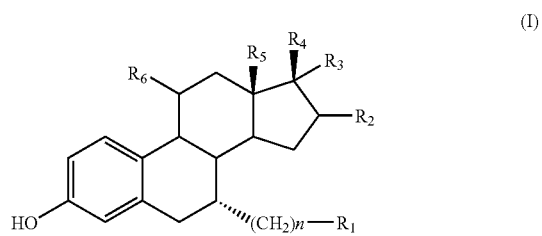

wherein
    n is an integer ranging from 3 to 14,
    $R_1$ is selected from the group consisting of Br, Cl, I, free base or a salt form of isothiouronium, or SH;
    $R_2$ is either hydrogen, $C_{1-6}$ alkyl, hydroxyl, protected hydroxy, or halo;
    $R_3$ is either hydrogen, $C_{1-6}$ alkyl, $C_{2-6}$ alkenyl, or $C_{2-6}$ alkynyl;
    $R_4$ is either hydroxy, or a $C_{1-6}$ acyloxy;
    $R_5$ is $C_{1-6}$ alkyl; and
    $R_6$ is either hydrogen, $C_{1-6}$ alkyl, hydroxyl, protected hydroxy, or halo.
    Preferably, n is 9, $R_1$ is Br, $R_2$, $R_3$, and $R_6$ are hydrogens, $R_4$ is hydroxy and $R_5$ is methyl. Said compound of formula (I) correspond to compound 9354 in FIG. 7.
    Preferably, n is 9, $R_1$ is Br, $R_2$, $R_3$, and $R_6$ are hydrogens, $R_4$ is acetyloxy and $R_5$ is methyl. Said compound of formula (I) correspond to compound 9342 in FIG. 6.
    Preferably, n is 9, $R_1$ is a hydrobromide salt of isothiouronium, $R_2$, $R_3$, and $R_6$ are hydrogens, $R_4$ is acetyloxy and $R_5$ is methyl. Said compound of formula (I) correspond to compound 9361 in FIG. 8.
    Preferably, n is 9, $R_1$ is a hydrobromide salt of isothiouronium, $R_2$, $R_3$, and $R_6$ are hydrogens, $R_4$ is hydroxy and $R_5$ is methyl. Said compound of formula (I) correspond to compound 9388 in FIG. 9.
    Preferably, n is 9, $R_1$ is SH, $R_2$, $R_3$, and $R_6$ are hydrogens, $R_4$ is acetyloxy and $R_5$ is methyl. Said compound of formula (I) correspond to compound 9362 in FIG. 8.
    Preferably, n is 9, $R_1$ is SH, $R_2$, $R_3$, and $R_6$ are hydrogens, $R_4$ is hydroxy and $R_5$ is methyl. Said compound of formula (I) correspond to compound 9389 in FIG. 9.
    Another aspect of the present invention is a compound of formula Compound 9341 (in Figure 5)

Another aspect of the present invention is a process for preparing the compound of formula (II), (II)

comprising:
    a) combining a 19-nor-androsta-4,6-diene-3-one of formula (III)

(III)

with an etheral solvent, to obtain a solution; and
    b) adding to the solution of step a), in a drop-wise manner, a solution of the compound of formula (IV)

(IV)

in an etheral solvent to obtain a reaction mixture.

wherein
    n is an integer ranging from 3 to 14,
    X is either O or S;
    $R_1$ is a $C_{1-10}$ haloalkyl or a hydroxy protecting group;
    $R_2$, $R_3$, $R_5$ and $R_6$ are as defined above;
    $R_4$ is a $C_{1-6}$ acyloxy; and
    z is a metal halide of the formula $R_7M$, wherein
    M is a metal atom; and
    $R_7$ is a halogen atom;
    In one embodiment, the solution is cooled to a temperature of about −60° C. to about 30° C.
    In one embodiment, the method further comprises quenching the reaction mixture.
    In one embodiment, the invention further comprises recovering the compound of formula (II).
    After combining the compound of formula (IV) and the compound of formula (III), the resulting reaction mixture can be analyzed using conventional methods, known to those skilled in the art, to determine completion of the reaction. For example, the reaction mixture may be analyzed by thin layer chromatography (TLC), high pressure liquid chromatography (HPLC), gas chromatography (GC), mass spectrometry (MS), or nuclear magnetic resonance (NMR).
    In one embodiment, the addition of the compound of formula (IV) to the solution of the compound of formula (III) is done over a time period of at least about 1 minute. Typically, the addition of the compound of formula (IV) to the solution of the compound of formula (III) is done over a time period of at least about 30 minutes, preferably at least about 60 minutes, more preferably at least about 90 minutes, and most preferably at least about 120 minutes. Preferably, the addition is slow enough to prevent any substantiative color changes in the mixture. It was found that the slower the addition, the better the isomer ratio obtained (other factors being unchanged). The addition time, however, may be governed by practical concerns (such as efficient use of available reactors) and it is not usually worthwhile to extend the addition period beyond 5 hours.
    In another embodiment, addition of the compound of formula (IV) to the solution of the compound of formula (III) is done at a specified rate, i.e., mol equivalents of compound of formula (IVi) per equivalent of compound of formula (III) per time unit. For example, the average rate of adding the compound of formula (IV) to the solution of the compound of formula (III) can range from about 0.001 mol equivalents to about 1 mol equivalents of compound of formula (IV) per equivalent of compound of formula (III) per minute. Preferably, the average rate of addition ranges from about 0.002 to about 0.100 mol equivalents of compound of formula (IV) per equivalent of compound of formula (III) per minute. More preferably, the average rate of addition ranges from about 0.005 to about 0.020 mol equivalents of compound of formula (IV) per equivalent of compound of formula (III) per minute.

Preferably, n is 9, X is O, $R_1$ is tertbutyl-dimethylsilyl (TBDMS), $R_2$, $R_3$ and $R_6$ are hydrogens, $R_4$ is acetyloxy and $R_5$ is methyl. Said compound of formula (III) corresponds to Compound 9294 in FIG. 1, said compound of formula (IV) corresponds to Compound 9318 in FIG. 1, and the obtained compound of formula (II) corresponds to Compound 9295 in FIG. 1.

Figure 2:
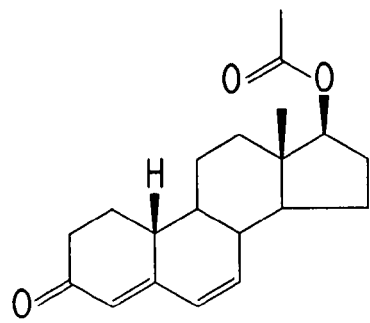
FIG. 2 is a schematic showing a method for making an intermediate, useful in the preparation of fulvestrant, according to the method of the invention.
Figure 2:
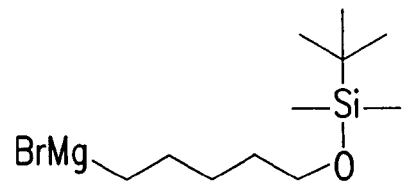
Figure 2:
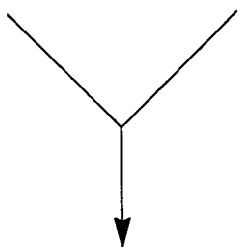
Figure 2:
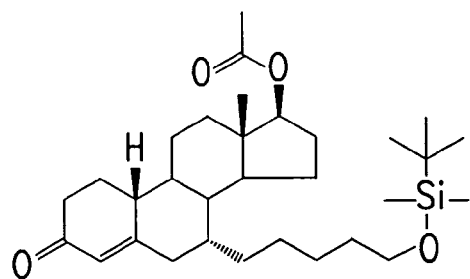

Alternatively, n is 5, X is O, $R_1$ is TBDMS, $R_3$ and $R_6$ are hydrogens, $R_4$ is acetyloxy and $R_5$ is methyl. Said compound of formula (III) corresponds to Compound 9294 in FIG. 2, said compound of formula (IV) corresponds to Compound 9339 in FIG. 2, and the obtained compound of formula (II) corresponds to Compound 9340 in FIG. 2.

Alternatively, n is 9, X is S, $R_1$ is —$(CH_2)_3CF_2CF_3$, $R_2$, $R_3$ and $R_6$ are hydrogens, $R_4$ is acetyloxy and $R_5$ is methyl. Said compound of formula (III) corresponds to Compound 9294 in FIG. 3, said compound of formula (IV) corresponds to Compound 9330 in FIG. 3, and the obtained compound of formula (II) corresponds to Compound 9331 in FIG. 3.

M in the compound of formula (IV) is a metal atom selected from the group consisting of magnesium, zinc, aluminum, copper, copper-lithium (i.e., a lithium dialkylcopper reagent), and titanium. The preferred metal atom is Mg. $R_7$ is a halogen atom selected from the group consisting of Cl, Br and I. Preferably, $R_7$ is Br.

When the metal is Mg, a copper catalyst should be used, preferably of the form Cu(I)Y, wherein Y is Cl, Br or I, and most preferably Cu(I)Cl.

The compound of formula (II) obtained by this method has a ratio of 7α- to 7β-epimer of about 2.5:1 to about 12.1:1.

In one embodiment, the compound of formula (II), has a ratio of 7α to 7β epimer (isomer ratio) of at least about 3:1. Preferably, the compound of formula (II) has a 7α to 7β ratio of at least about 7:1. More preferably, the compound of formula (II) has a 7α to 7β ratio of at least about 10:1. Most preferably, the compound of formula (II) has a 7α to 7β ratio of at least about 12:1.

The etheral solvent may be selected from the group consisting of: diethyl ether, THF and glyme. The preferred etheral solvent is THF.

Preferably, the solution of step b) is cooled to a temperature of about −20° C. to about −10° C.

The etheral solution of the compound of the formula (IV) is added in a dropwise manner, in order to avoid a local accumulation of it. The reaction mixture is stirred constantly, for the same reason. The dropwise addition of the compound of formula (IV) is what renders the high 7α/7β-epimer ratio.

The reaction mixture in step d) may be quenched by one of the reagents selected from the group consisting of: $NH_4Cl$, HCl, water, acetic acid and a mixture of $NH_4Cl$ with $NH_4OH$. The preferred reagent is acetic acid.

The compound of formula (II) may be recovered by any method known in the art. Preferably, traces of the used catalyst are removed, for example, by reaction with ammonium, followed by separation of the compound of formula (II) from the reaction mixture, for example, by evaporation of the solvents. The compound of formula (II) may be purified by any methods known in the art, such as chromatography.

Compounds 9295 and 9331, obtained as described above, may be further converted to fulvestrant.

Another aspect of the present invention is a process for preparing the compound of formula (V),

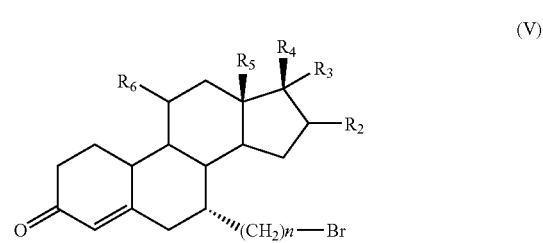

(V)

comprising combining a compound of formula (II)

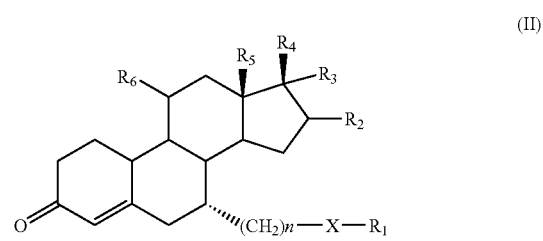

(II)

with acetonitrile and triphenylphosphine dibromide for a sufficient amount of time for conversion into the compound of formula (V)

wherein n is an integer ranging from 3 to 14,

X is O;

$R_1$ is a hydroxy protecting group;

$R_2$, $R_3$, $R_5$ and $R_6$ are as defined above; and $R_4$ is a $C_{1-6}$ acyloxy;

Preferably, n is 9, X is O, $R_1$ is tertbutyl-dimethylsilyl (TBDMS), $R_2$, $R_3$ and $R_6$ are hydrogens, $R_4$ is acetyloxy and $R_5$ is methyl. Said compound of formula (II) corresponds to Compound 9295 in FIG. 4, and said compound of formula (V) corresponds to Compound 9341 in FIG. 4.

Preferably, the compound of formula (II) is combined with the acetonitrile and triphenylphosphine dibromide at a temperature of about 10° C. to about 12° C. The compound of formula (V) may be obtained by any methods known in the art, and then it may be further purified by dissolution in toluene and removal of the by-products formed during the reaction.

Figure 5:
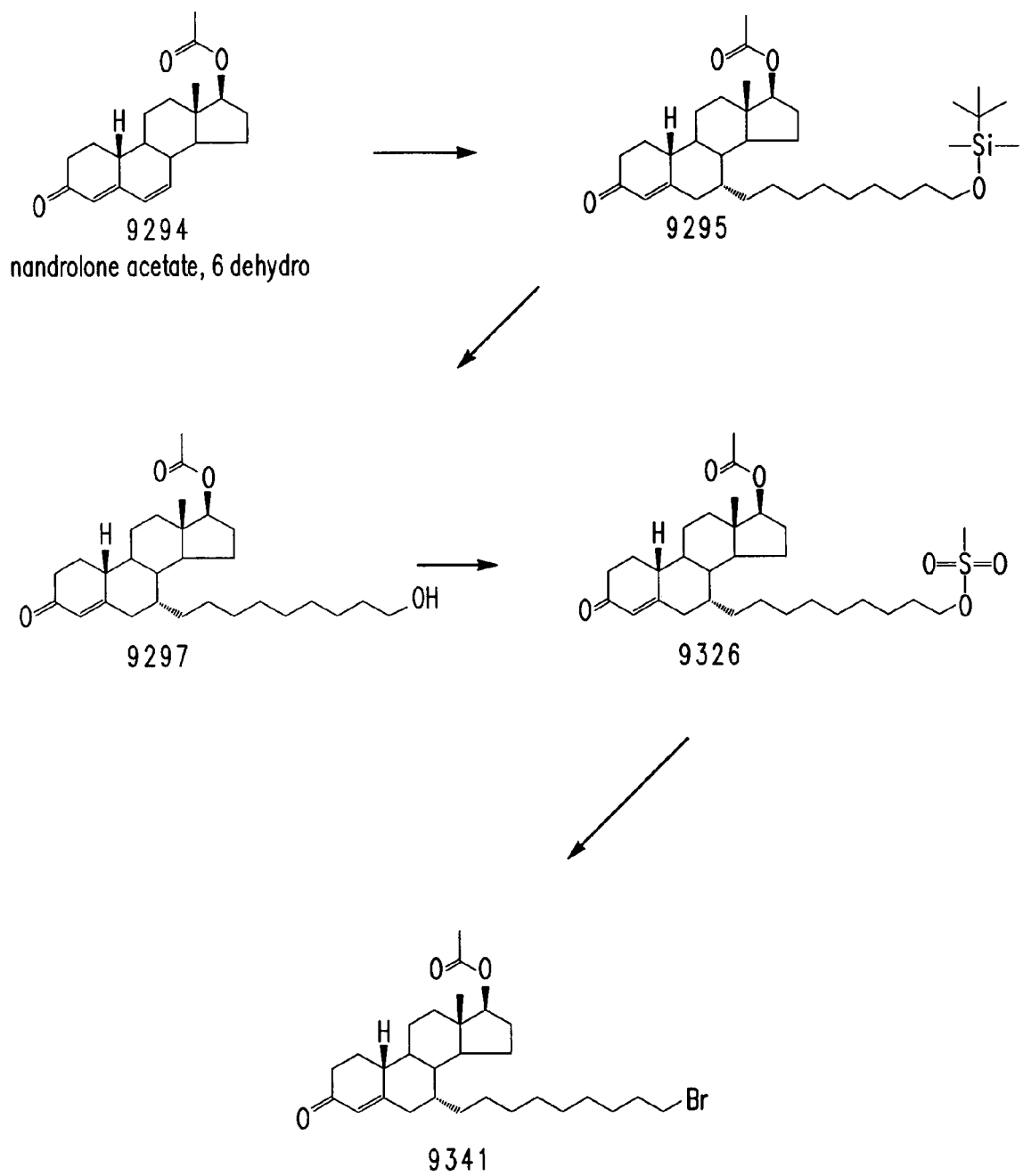
FIG. 5 is a schematic showing a method for making an intermediate, useful in the preparation of fulvestrant, according to the method of the invention.

The compound of formula (V) may be also prepared via the formation of intermediates, as depicted in FIG. 5.

Compound 9341, obtained as described above, may be further converted to fulvestrant.

Another aspect of the present invention is a process for preparing the compound of formula (VI)

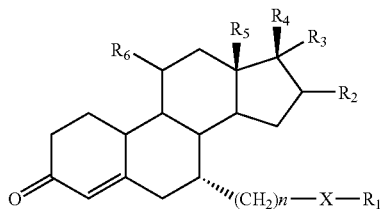

wherein $R_4$ is hydroxy, comprising combining the compound of formula (VI), wherein $R_4$ is a $C_{1-6}$ acyloxy, with a $C_{1-6}$ alcohol and mineral acid, at a temperature of about 50° C. to about 70° C.

Preferably, $R_2$, $R_3$ and $R_6$ are hydrogens, and $R_5$ is methyl. Said compound of formula (VI), wherein $R_4$ is a acetyloxy corresponds to Compound 9342 in FIG. 7, and said compound of formula (VI) wherein $R_4$ is hydroxy corresponds to Compound 9354 in FIG. 7.

Preferably, the mineral acid is HBr. Preferably, the temperature of the reaction is about 60° C.

Compound 9354, obtained as described above, may be further converted to fulvestrant.

A further aspect of the present invention is a process for preparing the compound of the formula (I)

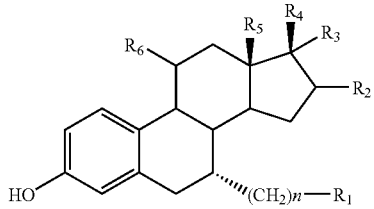

comprising combining the compound of formula (VI)

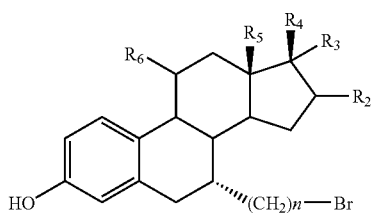

with a solvent selected from a $C_{1-6}$ aromatic hydrocarbon, a straight or branched $C_{1-4}$ alcohol, a $C_{1-4}$ alkyl amide and mixtures thereof and thiourea; and recovering the compound of formula (I)

wherein
n is an integer ranging from 3 to 14,
$R_1$ is a free base or a salt form of isothiouronium;
$R_2$, $R_3$, $R_5$ and $R_6$ are as defined above; and
$R_4$ is either hydroxy or $C_{1-6}$ acyloxy.

Preferably, n is 9, $R_1$ is a hydrobromide salt of isothiouronium, $R_2$, $R_3$ and $R_6$ are hydrogens, $R_4$ is acetyloxy and $R_5$ is methyl. Said compound of formula (VI) corresponds to Compound 9342 in FIG. 8, and said compound of formula (I) corresponds to Compound 9361 in FIG. 8.

Preferably, n is 9, $R_1$ is a hydrobromide salt of isothiouronium, $R_2$, $R_3$ and $R_6$ are hydrogens, $R_4$ is hydroxy and $R_5$ is methyl. Said compound of formula (VI) corresponds to Compound 9354 in FIG. 9, and said compound of formula (I) corresponds to Compound 9388 in FIG. 9.

A $C_{1-6}$ aromatic hydrocarbon may be toluene, xylene or benzene. A straight or branched $C_{1-4}$ alcohol may be methanol, ethanol, propanol, isopropanol or butanol. A $C_{1-4}$ alkyl amide may be dimethylacetamide. Most preferably the solvent a mixture of toluene and isopropanol or dimethylacetamide.

Compounds 9361 and 9388, obtained as described above, may be further converted to fulvestrant.

One aspect of the present invention is a process for preparing the compound of the formula (VII)

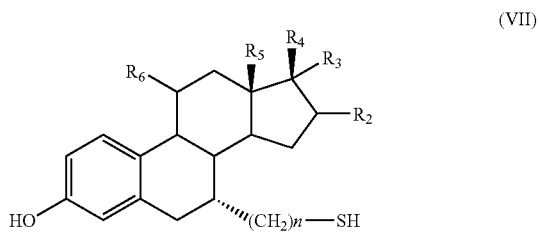

comprising combining a compound of the formula (I)

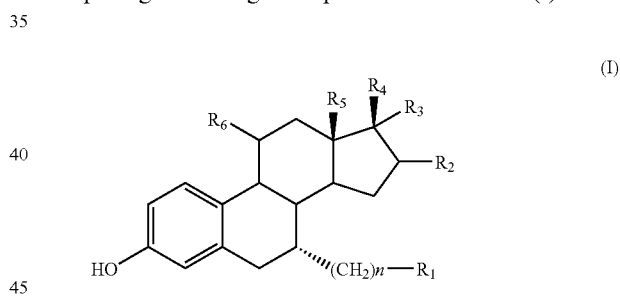

with a base in the presence of an apolar protic organic solvent at ambient temperature;
wherein
n is an integer ranging from 3 to 14,
$R_1$ is a free base or a salt form of isothiouronium;
$R_2$, $R_3$, $R_5$ and $R_6$ are as defined above; and
$R_4$ is either hydroxy or $C_{1-6}$ acyloxy.

Preferably, n is 9, $R_1$ is a hydrobromide salt of isothiouronium, $R_2$, $R_3$ and $R_6$ are hydrogens, $R_4$ is acetyloxy and $R_5$ is methyl. Said compound of formula (VII) corresponds to Compound 9362 in FIG. 8, and said compound of formula (I) corresponds to Compound 9361 in FIG. 8.

Preferably, n is 9, $R_1$ is a hydrobromide salt of isothiouronium, $R_2$, $R_3$ and $R_6$ are hydrogens, $R_4$ is hydroxy and $R_5$ is methyl. Said compound of formula (VII) corresponds to Compound 9389 in FIG. 9, and said compound of formula (I) corresponds to Compound 9388 in FIG. 9.

Preferably, the base is an alkali metal base such as NaOH and KOH. Most preferably, the base is NaOH. The aprotic polar organic solvent may be dimethylacetamide or acetonitrile. Preferably, the aprotic polar organic solvent is dimethylacetamide.

Compounds 9362 and 9389, obtained as described above, may be further converted to fulvestrant.

Another aspect of the present invention is a process for preparing the compound of the formula (I)

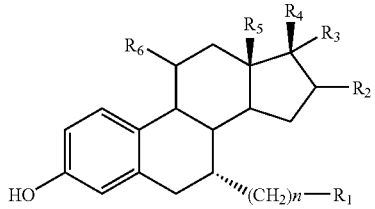

(I)

comprising combining the compound of formula (VII)

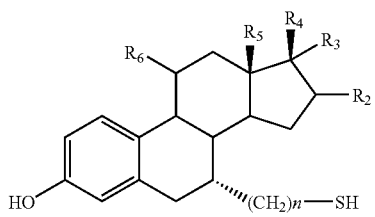

(VII)

with 4,4,5,5,5-pentafluoropentane-1-ol mesylate, followed by combining the obtained reaction mixture with a base in the presence of an organic solvent;

wherein n is an integer ranging from 3 to 14, $R_1$ is —S—$(CH_2)_3CF_2CF_3$ $R_2$, $R_3$, $R_5$ and $R_6$ are as defined above; and $R_4$ is either hydroxy or $C_{1-6}$ acyloxy.

In one embodiment, the compound of formula (VII) and 4,4,5,5,5-pentafluoropentane-1-ol mesylate are contacted at ambient temperature.

Preferably, n is 9, $R_2$, $R_3$ and $R_6$ are hydrogens, $R_4$ is acetyloxy and $R_5$ is methyl. Said compound of formula (I) corresponds to Compound 9363 in FIG. 8, and said compound of formula (VII) corresponds to Compound 9362 in FIG. 8.

Preferably, n is 9, $R_2$, $R_3$ and $R_6$ are hydrogens, $R_4$ is acetyloxy and $R_5$ is methyl. Said compound of formula (I) corresponds to Compound 9304 in FIG. 9, and said compound of formula (VII) corresponds to Compound 9389 in FIG. 9.

Preferably, the base is an alkali metal base such as NaOH and KOH. Most preferably, the base is KOH. Preferably, the organic solvent is a $C_{1-6}$ alcohol. Most preferably, the organic solvent is methanol.

Compounds 9363 and 9304, obtained as described above, may be further converted to fulvestrant.

Another aspect of the invention is a process for preparing fulvestrant comprising a) combining compound of formula 9294

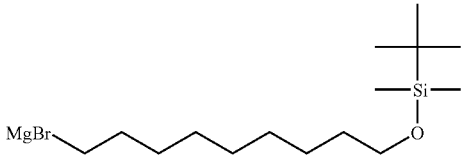

9294 with an etheral solvent, to obtain a solution;

b) adding to the solution of step a), in a drop-wise manner, a solution of the compound of formula 9318

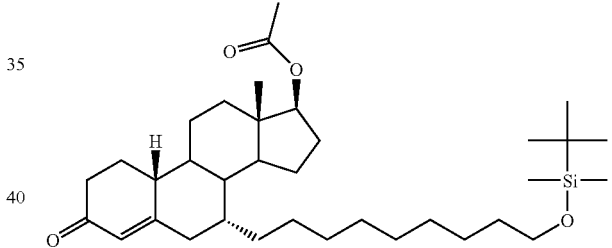

9318 in an etheral solvent to obtain a first reaction mixture comprising a compound of formula 9295;

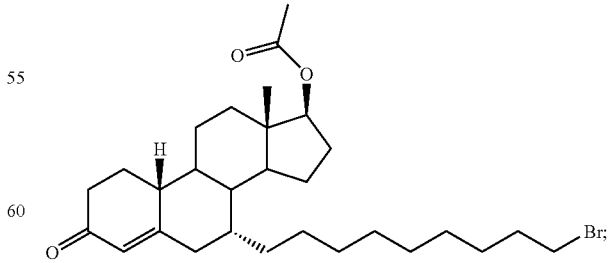

c) quenching the first reaction mixture;

d) recovering compound 9295;

e) combining compound 9295 with acetonitrile and triphenylphosphine dibromide for a time sufficient to convert compound 9295 into a compound of formula 9341

9341 f) aromatizing the A ring of compound 9341 by reacting compound 9341 with a mixture of lithium bromide and copper bromide in acetonitrile to obtain a compound of formula 9342

9342

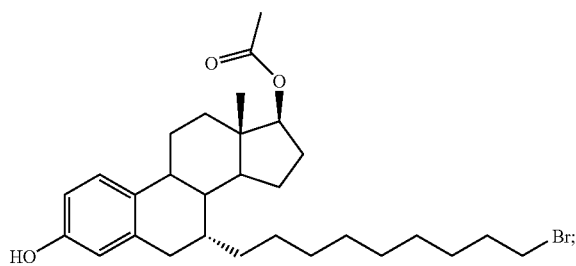

g) combining compound 9342 with $C_{1-6}$ alcohol and a mineral acid, at a temperature of about 50° C. to about 70° C. to obtain a compound of formula 9354

9354

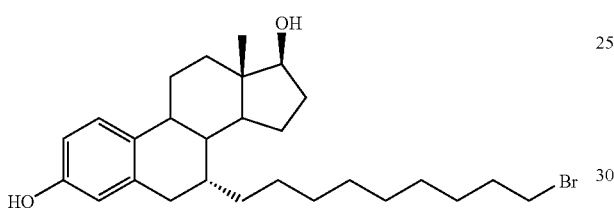

h) combining compound 9354 with a compound of formula 9383

HS(CH$_2$)$_3$CF$_2$CF$_3$   9383;

in the presence of an amide and an alkali base to obtain compound 9304

9304

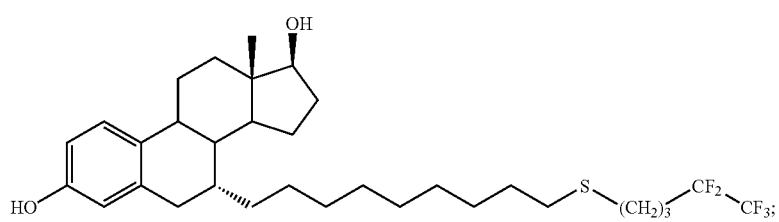

and i) combining compound 9304 and a mixture of a $C_{1-4}$ alcohol and an etheral solvent with an aqueous solution of an oxidizing agent at a temperature of about 5° C. for about 12 hours to provide fulvestrant.

Fulvestrant can be recovered by any methods known in the art, such as evaporating the solvents, and can be further purified by crystallization from a $C_{1-6}$ aromatic hydrocarbon.

In one embodiment, the solution of the compound of formula 9318 is added to the solution of the compound of formula 9294 at a temperature of about −60° C. to about 30° C.

Another aspect of the invention is a process for preparing fulvestrant comprising:

a) combining compound of formula 9294

9294

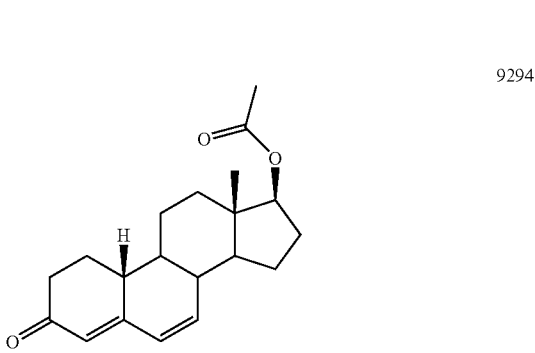

with an etheral solvent, to obtain a solution;

b) adding to the solution of step a), in a drop-wise manner, a solution of the compound of formula 9318

9318

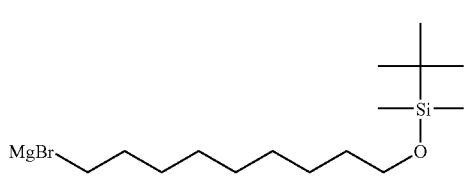

in an etheral solvent to obtain a first reaction mixture comprising a compound of formula 9295;

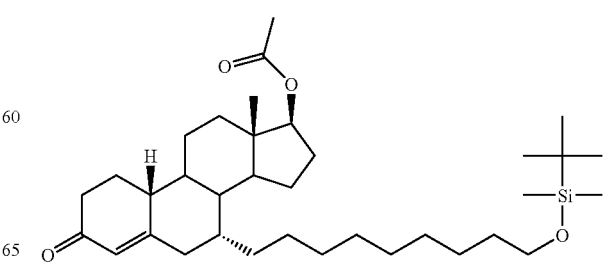

c) quenching the first reaction mixture;
d) recovering compound 9295;
e) combining compound 9295 with acetonitrile and triphenylphosphine dibromide for a time sufficient to convert compound 9295 into a compound of formula 9341

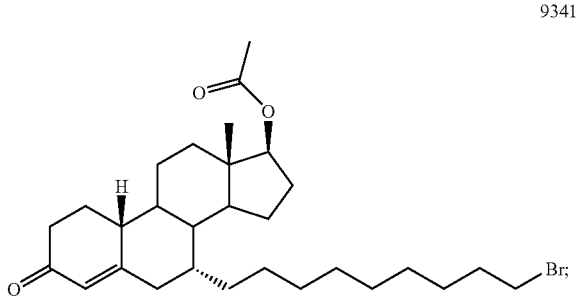

f) aromatizing the A ring of compound 9341 by reacting compound 9341 with a mixture of lithium bromide and copper bromide in acetonitrile to obtain a compound of formula 9342

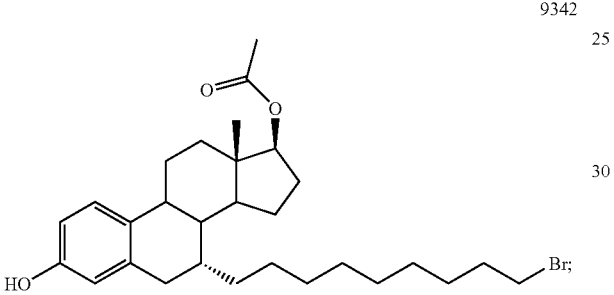

g) combining compound 9342 with $C_{1-6}$ alcohol and a mineral acid, at a temperature of about 50° C. to about 70° C. to obtain a compound of formula 9354

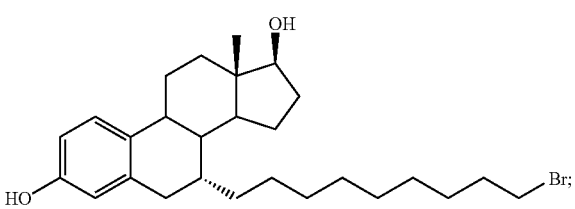

h) combining compound 9354 with a solvent selected from a $C_{1-6}$ aromatic hydrocarbon, a straight or branched $C_{1-4}$ alkyl amide and mixtures thereof and thiourea to provide a compound of formula 9388

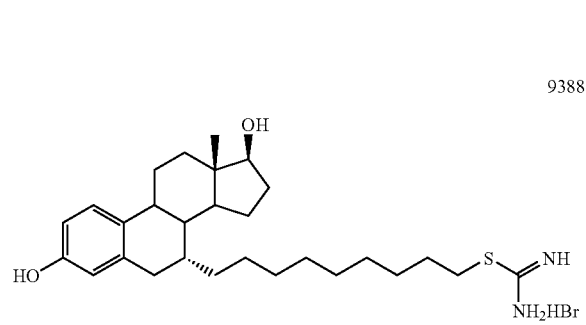

and recovering compound 9388;

i) combining compound 9388 with a base at ambient temperature to obtain a compound of formula 9389

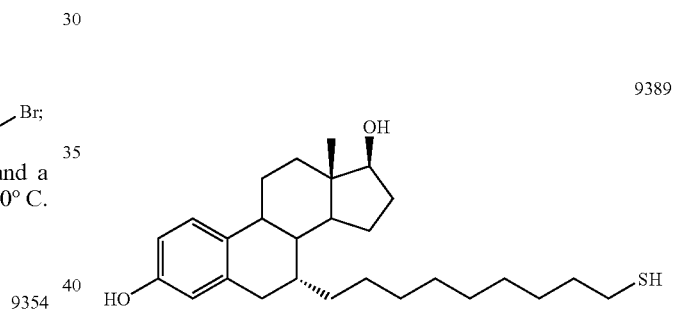

j) combining compound 9389 with 4,4,5,5,5-pentafluoropenatane-1-ol mesylate at an ambient temperature to provide a second reaction mixture and then combining the second reaction mixture with a base to obtain a compound of formula 9304

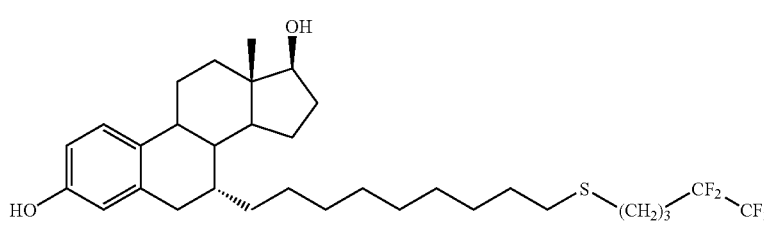

and k) combining compound 9304 and a mixture of a $C_{1-4}$ alcohol and an etheral solvent with an aqueous solution of an oxidizing agent at a temperature of about 5° C. for about 12 hours to provide fulvestrant.

Fulvestrant can be recovered by any methods known in the art, such as evaporating the solvents, and can be further purified by crystallization from a $C_{1-6}$ aromatic hydrocarbon.

In one embodiment, the solution of the compound of formula 9318 is added to the solution of the compound of formula 9294 at a temperature of about −60° C. to about 30° C.

Another aspect of the invention is a process for preparing fulvestrant comprising:

a) combining compound of formula 9294

9294

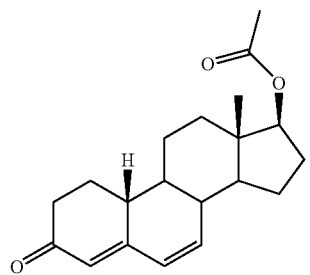

with an etheral solvent, to obtain a solution;

b) adding to the solution of step a), in a drop-wise manner, a solution of the compound of formula 9318

9318 in an etheral solvent to obtain a first reaction mixture comprising a compound of formula 9295;

c) quenching the first reaction mixture;

d) recovering compound 9295;

e) combining compound 9295 with acetonitrile and triphenylphosphine dibromide for a time sufficient to convert compound 9295 into a compound of formula 9341

9341 f) aromatizing the A ring of compound 9341 by reacting compound 9341 with a mixture of lithium bromide and copper bromide in acetonitrile to obtain a compound of formula 9342

9342 g) combining compound 9342 with a compound of formula 9383

HS(CH$_2$)$_3$CF$_2$CF$_3$    9383;

to provide a compound of formula 9363

9363 h) combining at ambient temperature, compound 9363 and a $C_{1-4}$ alcohol with an alkali base to obtain compound 9304

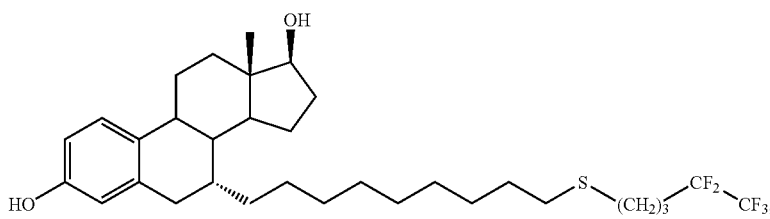

9304 and i) combining compound 9304 and a mixture of a $C_{1-4}$ alcohol and an etheral solvent with an aqueous solution of an oxidizing agent at a temperature of about 5° C. for about 12 hours to provide fulvestrant.

Fulvestrant can be recovered by any methods known in the art, such as evaporating the solvents, and can be further purified by crystallization from a $C_{1-6}$ aromatic hydrocarbon.

In one embodiment, the solution of the compound of formula 9318 is added to the solution of the compound of formula 9294 at a temperature of about −60° C. to about 30° C.

Another aspect of the invention is a process for preparing fulvestrant comprising a) combining compound of formula 9294

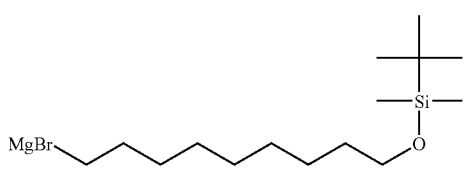

9294 with an etheral solvent, to obtain a solution;

b) adding to the solution of step a), in a drop-wise manner, a solution of the compound of formula 9318

9318 in an etheral solvent to obtain a first reaction mixture comprising a compound of formula 9295;

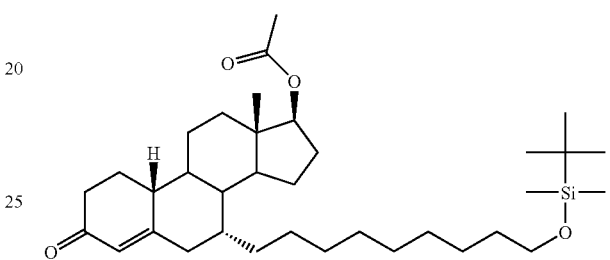

c) quenching the first reaction mixture;
d) recovering compound 9295;
e) combining compound 9295 with acetonitrile and triphenylphosphine dibromide for a time sufficient to convert compound 9295 into a compound of formula 9341

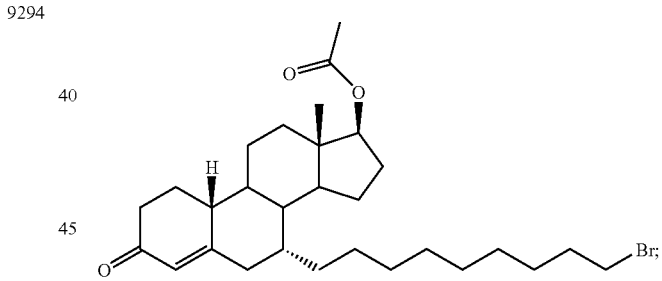

9341 f) aromatizing the A ring of compound 9341 by reacting compound 9341 with a mixture of lithium bromide and copper bromide in acetonitrile to obtain a compound of formula 9342

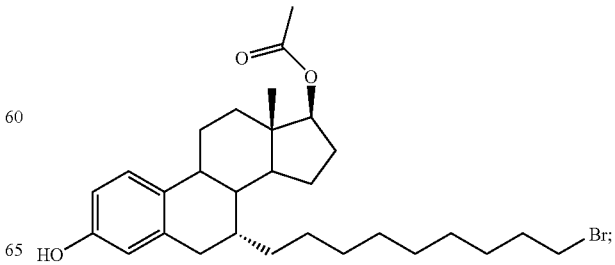

9342 g) combining compound 9342 with a solvent selected from a $C_{1-6}$ aromatic hydrocarbon, a straight or branched $C_{1-4}$ alkyl amide and mixtures thereof and thiourea to provide a compound of formula 9361

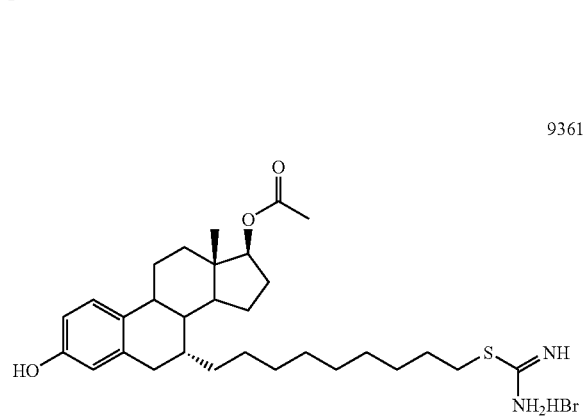

9361 and recovering compound 9361.

h) combining compound 9361 with a base at an ambient temperature to obtain a compound of formula 9362

9362 i) combining compound 9362 with 4,4,5,5,5-pentafluoro-penatane-1-ol mesylate (compound 9360) at ambient temperature to provide a second reaction mixture followed by combining the second reaction mixture with a base to obtain a compound of formula 9363

9363 j) combining at ambient temperature compound 9363 and a $C_{1-4}$ alcohol with an alkali base to obtain a compound of formula 9304

9304 and k) combining compound 9304 and a mixture of a $C_{1-4}$ alcohol and an etheral solvent with an aqueous solution of an oxidizing agent at a temperature of about 5° C. for about 12 hours to provide fulvestrant.

Fulvestrant can be recovered by any methods known in the art, such as evaporating the solvents, and can be further purified by crystallization from a $C_{1-6}$ aromatic hydrocarbon.

In one embodiment, the solution of the compound of formula 9318 is added to the solution of the compound of formula 9294 at a temperature of about −60° C. to about 30° C.

Another aspect of the invention is a process for preparing fulvestrant comprising a) reacting a compound of formula 9363

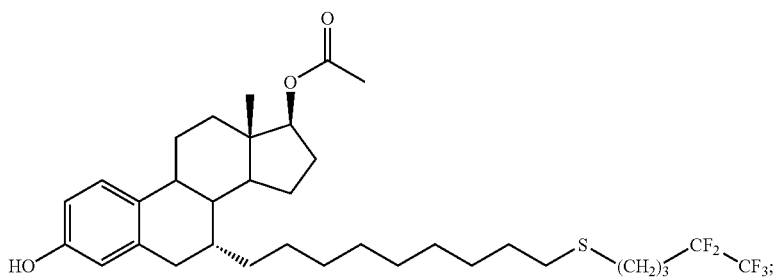

9363 with a mixture of a $C_{1-4}$ alcohol and an etheral solvent with an aqueous solution of an oxidizing agent at a temperature of about 5° C. for about 12 hours to provide a compound of formula 9368

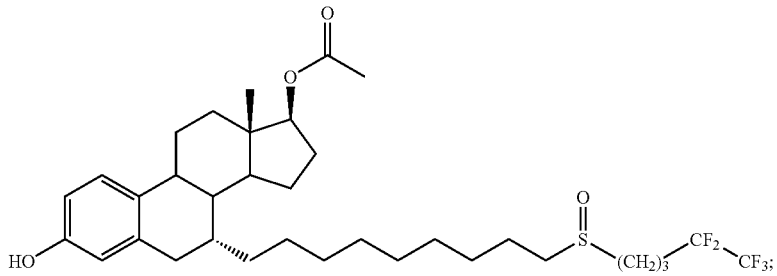

9368 and b) combining at ambient temperature compound 9368 and a $C_{1-4}$ alcohol with an alkali base to obtain fulvestrant.

Figure 13:
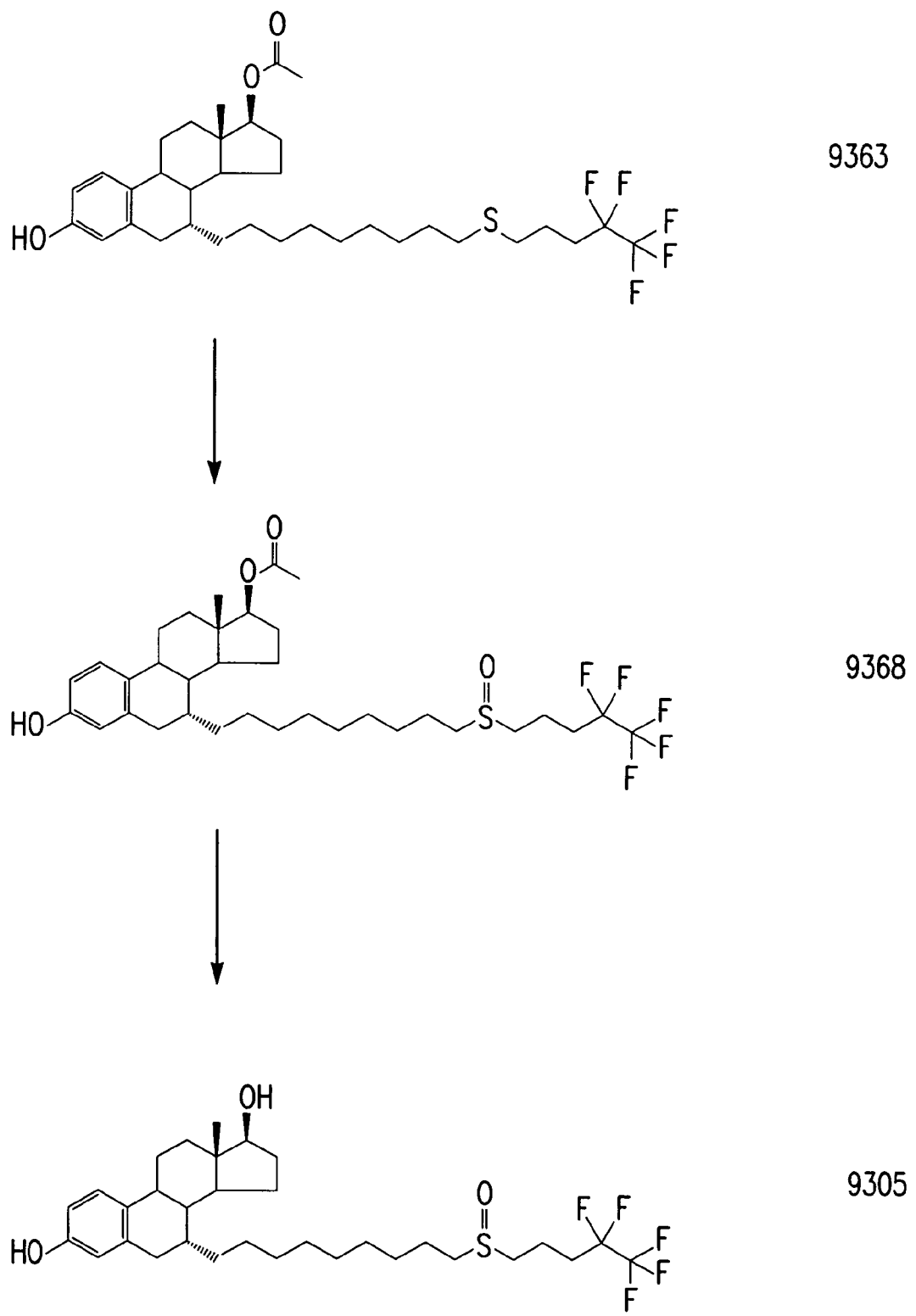
FIG. 13 is a schematic showing a method for making fulvestrant according to the method of the invention.

This method is depicted schematically in FIG. 13.

The compound of formula 9363 can be made by any method of the invention.

EXAMPLES

Comparative Example Repeating EP 138504

Following the method of Example 1 of EP 138504, to the Grignard reagent, Cp 9318, formed from 24.2 grams of 9-bromo-1-nonanol TBDMS (i.e., 9-(dimethyl-t-butylsiloxy) nonyl bromide), cooled to −30° C., were added 6.6 grams of copper (I) iodide. After stirring for 10 minutes a solution of 10 grams of 17β hydroxy estra 4,6 diene 3 one acetate, Cp 9294 (i.e., 6-dehydro-19-nortestosterone acetate), in tetrahydrofuran was added, and stirring continued for 90 minutes. After quenching with acetic acid, the product 17β-hydroxy-7α-[9-[[1,1-dimethylethyl)dimethylsilyl]oxy]nonyl]-estr-4-en-3-oneacetate, Cp 9295, was examined by HPLC analysis and found to have a 7α/7β ratio of 2.3:1.

Comparative Example Repeating WO 02/32922

Following the method of Example 2 of WO 02/32922, the 7α/7β ratio obtained was 2.5:1.

Example 1

Preparation of the Grignard Reagent Cp 9318 (9-(dimethyl-tert-butylsilyloxy)nonyl Magnesium Bromide)

To a mixture of 100 g of 1-bromononanol, 33 g of imidazole and 250 g of dimethylformamide was added 70.2 g of tert-butyl-chlorodimethylsilane and the reaction mixture was stirred for 2 hours.

The mixture was diluted with 750 g of water and 220 g of toluene, and the phases separated. The aqueous phase was re-extracted with 90 g of toluene.

The combined organic phases were washed with 100 g of water, and evaporated under vacuum at 80°. The residue of 9-bromo-1-nonanol TBDMS was dissolved in 500 g of anhydrous tetrahydrofuran.

In a 2 L flask fitted with stirrer, heating bath, condenser, nitrogen atmosphere, and thermometer 10.88 g of magnesium turnings and 100 g of tetrahydrofuran were charged and heated up to 45°.

A small amount of 9-bromo-1-nonanol TBDMS was added to initiate the reaction, and then the remaining solution was added dropwise at such a rate as to maintain the reaction mixture at reflux.

When addition was finished the reaction mixture was refluxed for another hour, then cooled to about 40° C. and filtered under nitrogen through a sintered glass in-line filter (to remove some residual magnesium) and diluted to about 1.15 L. The solution of reagent was kept at room temperature under nitrogen.

Example 2

Preparation of Cp 9295 from Cp 9294 (Depicted in FIG. 1)

10 grams of nandrolone acetate, Cp 9294 (6 dehydro 17β hydroxy estra 4,6 diene 3 one acetate), was dissolved in 60 grams of tetrahydrofuran and 1.5 grams of copper (I) chloride added. The suspension was cooled under a nitrogen atmosphere to −20° C. and 117 grams of a ca. 0.39M solution of the Grignard reagent, Cp 9318, formed from 9-bromo-1-nonanol TBDMS (9-(dimethyl-tert-butylsilyloxy)nonyl magnesium bromide) was added dropwise over 120 minutes. 10 grams of acetic acid was then added, and stirring continued for 30 minutes at room temperature. The flask was then opened to the atmosphere and a solution of 10 grams of ammonium chloride plus 15 grams of a 25% ammonium hydroxide solution in 73 grams of water was added and stirring was continued for 2 hours. The phases were separated and the upper phase washed with a solution of 5 grams ammonium chloride in 37 grams of water. The upper phase was separated and the solvent was evaporated under reduced pressure to provide an oily residue which was dissolved in dichloromethane (100 grams) and further washed with 50 grams of water. The lower phase was separated and the solvent was evaporated under reduced pressure to provide an oil (26.0 grams) containing 16.9 grams of 17β-hydroxy-7α-[9-[[1,1-dimethylethyl)dimethylsilyl]oxy]nonyl]-estr-4-en-3-one acetate, Cp 9295, by HPLC assay (93% of theoretical) having a 7α/7β ratio of 12.1:1.

The oil was further purified by chromatography using 200 grams of silica gel, eluting with 5% ethyl acetate in toluene. The main fraction, after evaporation of the solvent, yielded Cp 9295 as an oil (16.8 grams) containing 15.9 grams of 17β-hydroxy-7α-[9-[[1,1-dimethylethyl)dimethylsilyl]oxy]nonyl]-estr-4-en-3-one acetate by HPLC assay (87.5%) having an 7-alpha/7-beta ratio of 96.4:3.6. A later fraction (0.5 grams) contained mainly the 7-β isomer (7α/7β ratio ca 1:3).

The rate of adding 9-(dimethyl-tert-butylsilyloxy)nonyl magnesium bromide, Cp 9318 was: 0.041 moles of 9-(dimethyl-tert-butylsilyloxy)nonyl magnesium bromide were added to 0.032 moles of nandrolone acetate in 120 minutes. This translates into 1.28 mol equivalents in 120 minutes, or an average of ca. 0.011 mol equivalents per minute.

Example 3

Preparation of Cp 9295 from Cp 9294 (Depicted in FIG. 1)

10 grams of nandrolone acetate (6 dehydro 17β hydroxy estra 4,6 diene 3 one acetate), Cp 9294, was dissolved in 54 grams of tetrahydrofuran and 1 gram of copper (I) chloride added. The suspension was cooled under nitrogen atmosphere to −20° C. and 146 grams of a 0.346M solution of 9-(dimethyl-tert-butylsilyloxy)nonyl magnesium bromide, Cp 9318, (i.e., the Grignard reagent from 9-bromo-1-nonanol TBDMS) was added dropwise over 75 minutes. 10 grams of acetic acid was added and stirring was continued for 30 minutes at room temperature. The flask was then opened to the atmosphere and a solution of 10 grams of ammonium chloride plus 15 grams of a 25% ammonium hydroxide solution in 73 grams of water was added and stirring was continued for 2 hours. The phases were separated and the upper phase was re-extracted with a solution of 5 grams ammonium chloride plus 0.5 grams of a 25% ammonium hydroxide solution in 37 grams of water. The upper phase was separated and the solvent was evaporated under reduced pressure to provide an oily residue that contained 16.2 grams of 17β-hydroxy-7α-[9-[[1,1-dimethylethyl)dimethylsilyl]oxy]nonyl]-estr-4-en-3-one acetate, Cp 9295, by HPLC assay (89% of theoretical) having a 7α/7β ratio of 9.2:1

Example 4

Preparation of Cp 9295 from Cp 9294 (Depicted in FIG. 1)

5 grams of nandrolone acetate (6 dehydro 17β hydroxy estra 4,6 diene 3 one acetate), Cp 9294, was dissolved in 60 grams of tetrahydrofuran and 0.5 grams of copper (I) bromide added. The suspension was cooled under nitrogen atmosphere to −15° C. and 90 grams of a ca. 0.39M solution of 9-(dimethyl-tert-butylsilyloxy)nonyl magnesium bromide, Cp 9318, (i.e., the Grignard reagent from 9-bromo-1-nonanol TBDMS) was added dropwise over 120 minutes. After another hour, 5.4 grams of acetic acid was added and stirring continued for 60 minutes at room temperature. The flask was then opened to the atmosphere and a solution of 7 grams of ammonium chloride plus 10 grams of a 25% ammonium hydroxide solution in 50 grams of water was added and stirring was continued for 12 hours. The phases were separated and the upper phase washed with a solution of 2 grams ammonium chloride in 10 grams of water. The upper phase was then separated and the solvent evaporated under reduced pressure to provide an oily residue that was dissolved in dichloromethane (100 grams) and further washed with 50 grams of water. The lower phase was separated and the solvent evaporated under reduced pressure to provide oil, Cp 9295, (18.0 grams) with a 7α/7β ratio of 7.1:1 by HPLC.

Example 5

Preparation of Cp 9295 from Cp 9294 (Depicted in FIG. 1)

5 grams of nandrolone acetate (6 dehydro 17β hydroxy estra 4,6 diene 3 one acetate, Cp 9294,) was dissolved in 50 grams of tetrahydrofuran and 2.5 grams of copper (I) iodide added. The suspension was cooled under nitrogen atmosphere to −20° C. and 85 grams of a ca. 0.30M solution of 9-(dimethyl-tert-butylsilyloxy)nonyl magnesium bromide, Cp 9318, (i.e., the Grignard reagent from 9-bromo-1-nonanol TBDMS) was added dropwise over 120 minutes while maintaining the temperature of the reaction mixture between −10° C. and −20° C. After the addition of 60 grams of the Grignard reagent the reaction was shown by HPLC analysis to be incomplete, but to contain the product 17β-hydroxy-7α-[9-[[1,1-dimethylethyl)dimethylsilyl]oxy]nonyl]-estr-4-en-3-one acetate, Cp 9295, with a 7α/7β ratio of 8.0:1. After complete addition and another hour of stirring, 4.5 grams of acetic acid was added, and stirring continued for 30 minutes at room temperature. The flask was then opened to the atmosphere and a solution of 7.5 grams of ammonium chloride in 80 grams of water was added and stirring was continued for 12 hours. The phases were separated and the upper phase was washed with a solution of 2 grams ammonium chloride in 10 grams of water. The upper phase was separated and the solvent evaporated under reduced pressure to provide oil (13.9 grams) with a 7α/7β ratio of 7.7:1 by HPLC.

Example 6

Figure 3:
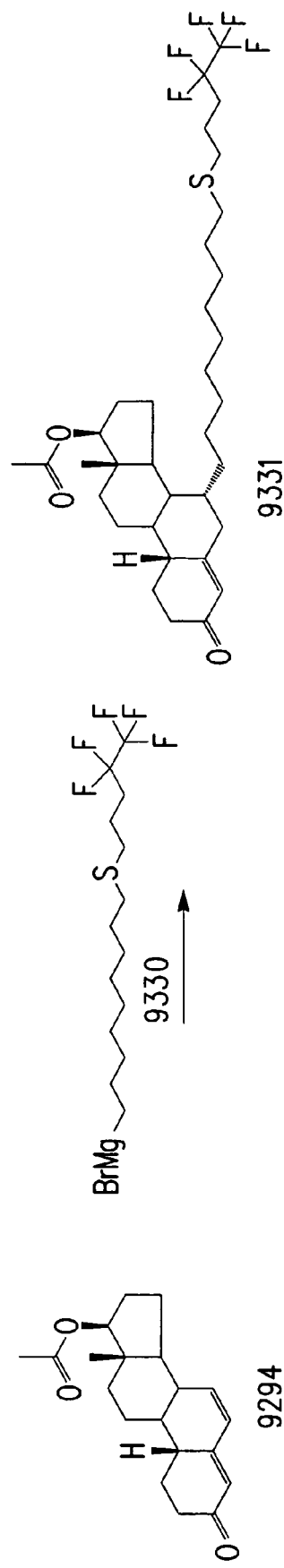
FIG. 3 is a schematic showing a method for making an intermediate, useful in the preparation of fulvestrant, according to the method of the invention.

Preparation of Cp 9331 from Cp 9294 (Depicted in FIG. 3)

10 grams of nandrolone acetate (6 dehydro 17β hydroxy estra 4,6 diene 3 one acetate), Cp 9294, are dissolved in 60 grams of tetrahydrofuran and 1.5 grams of copper (I) chloride are added. The suspension is cooled under nitrogen atmosphere to −20° C., and 117 grams of a ca. 0.39M solution of 9-[(4,4,5,5,5-pentafluoropentyl)thio]nonyl magnesium bromide, Cp 9330, are added dropwise over 120 minutes. 10 grams of acetic acid are then added, and stirring continued for 30 minutes at room temperature. The flask is then opened to the atmosphere and a solution of 10 grams of ammonium chloride plus 15 grams of a 25% ammonium hydroxide solution in 73 grams of water are added and stirring is continued for 2 hours. The phases are separated and the upper phase is washed with a solution of 5 grams ammonium chloride in 37 grams of water. The upper phase is then separated and the solvent evaporated to provide an oily residue which is dissolved in dichloromethane (100 grams) and is further washed with 50 grams of water. Evaporation of the lower phase gives an oil containing 17β-hydroxy-7α-[9-[(4,4,5,5,5-pentafluoropentyl)thio]nonyl]-estr-4-en-3-one acetate, Cp 9331, with a 7α/7β ratio of 9.1:1 by HPLC assay.

Example 7

Figure 4:
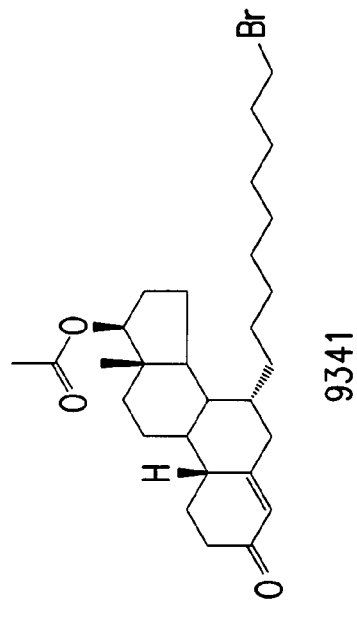
FIG. 4 is a schematic showing a method for making an intermediate, useful in the preparation of fulvestrant, according to the method of the invention.
Figure 4:
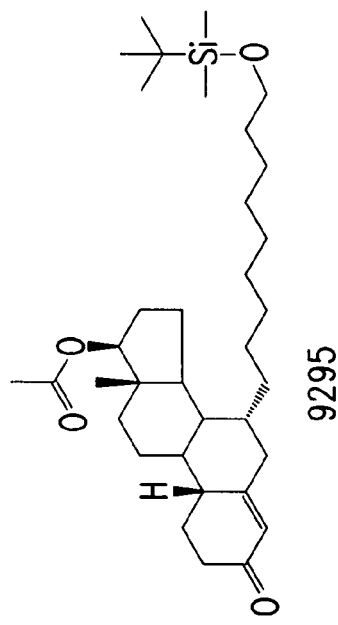

Preparation of Cp 9341 from Cp 9295—Direct Synthesis (Depicted in FIG. 4)

190 grams of crude Cp 9295 (17β-hydroxy-7α-[9-[[1,1-dimethylethyl)dimethylsilyl]oxy]nonyl]-estr-4-en-3-one acetate), prepared from 75 grams of 6-dehydronandrolone acetate using conditions of Example 4, are dissolved in 100 grams of acetonitrile and added to a suspension at 10-12° C. of triphenylphosphine dibromide (prepared by addition of 140 grams of bromine to 240 grams of triphenylphosphine in 1200 grams of acetonitrile). The temperature is allowed to rise to ambient temperature and after 0.5 hours conversion into Cp 9341 is complete by HPLC. The suspension is diluted with 1000 grams of toluene, neutralised with ca. 112 grams of ammonium hydroxide solution 25%, and the phases are separated. The upper (organic) phase is washed with water (100 g) and then evaporated to an oily residue. The residue is taken up in toluene and stirred at 5-10° C. in order to precipitate most of the triphenylphosphine oxide by-product. The by-product is filtered off and rinsed with toluene and the filtrate purified by chromatography on silica gel (1250 grams) eluting with toluene. Weight of pure Cp 9341 obtained: 87 g.

Example 7

Figure 8:
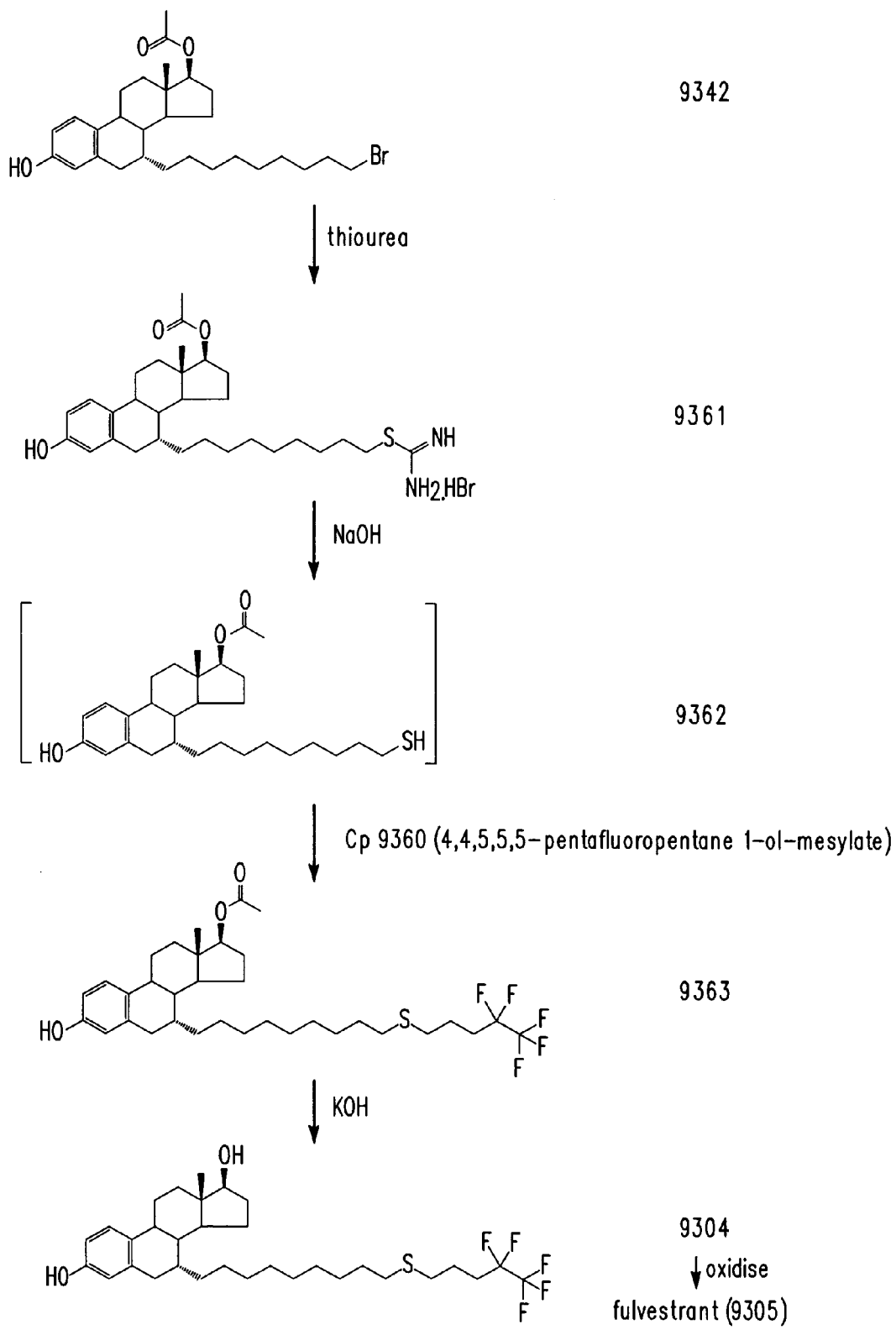
FIG. 8 is a schematic showing a method for making fulvestrant according to the method of the invention.

Preparation of Cp 9341 from Cp 9295—Indirect Synthesis (Depicted in FIG. 8)

190 grams of crude Cp 9295 (17β-hydroxy-7α-[9-[[1,1-dimethylethyl)dimethylsilyl]oxy]nonyl]-estr-4-en-3-one acetate), prepared from 75 grams of 6-dehydronandrolone acetate (Cp 9294) using conditions of Example 4, are dissolved in 750 grams of methanol and cooled to between 5° C. and 10° C. under nitrogen. The solution is treated with a solution of hydrochloric acid 32% (15 g) in water (45 g) and kept at 5° C. to 10° C. for 30-60 minutes. The reaction mixture is neutralised by charging a solution of ammonium hydroxide solution 25% (15 g) in distilled apyrogenic water (45 g) and evaporated under vacuum to an oily residue. The residue was dissolved in dichloromethane, extracted with water, and evaporated to an oily residue. Weight of crude Cp 9297 obtained: ca. 150 g.

The oily residue is dissolved in dichloromethane (975 g) and triethylamine (60 g), cooled to between 0° C. and 5° C., and treated at this temperature with methanesulfonyl chloride (48 g). The temperature of the reaction mixture is brought to between 20° C.-25° C. and the mixture is stirred at this temperature for 30 to 60 minutes.

With starting material absent, a solution of sodium chloride (75 g) in water (1125 g) is added and the mixture stirred for 2-3 hours at room temperature. The phases are separated and the lower (organic) phase again extracted with a solution of sodium chloride (75 g) in water (1125 g). The lower (organic) phase is evaporated at atmospheric pressure to an oily residue. Weight of crude Cp 9326 obtained: ca. 175 g.

The oily residue is dissolved in acetonitrile (375 g) and lithium bromide (41.2 g) added. The mixture is heated at 55-60° C. for 1.5-2 hours, and then evaporated under vacuum to an oily residue. The residue is dissolved in toluene (650 g) and the solution stirred at 35 to 40° C. with a solution of sodium chloride (75 g) in water (1125 g) for 0.5 hours. The phases are separated and the upper (organic) phase is washed with water (375 g) and then evaporated to an oily residue. Weight of crude Cp 9341 obtained: ca. 165 g.

If required, the product may be further purified by chromatography on silica gel (1120 grams) eluting with toluene. Weight of pure Cp 9341 obtained: 95 g.

Example 9

Figure 6:
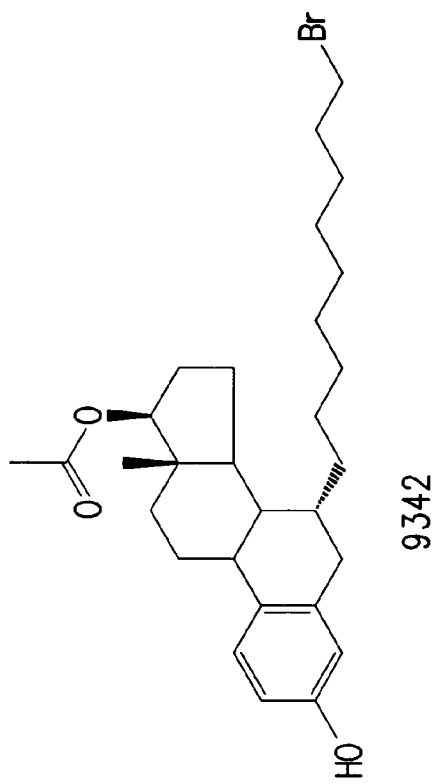
FIG. 6 is a schematic showing a method for making an intermediate, useful in the preparation of fulvestrant, according to the method of the invention.
Figure 6:
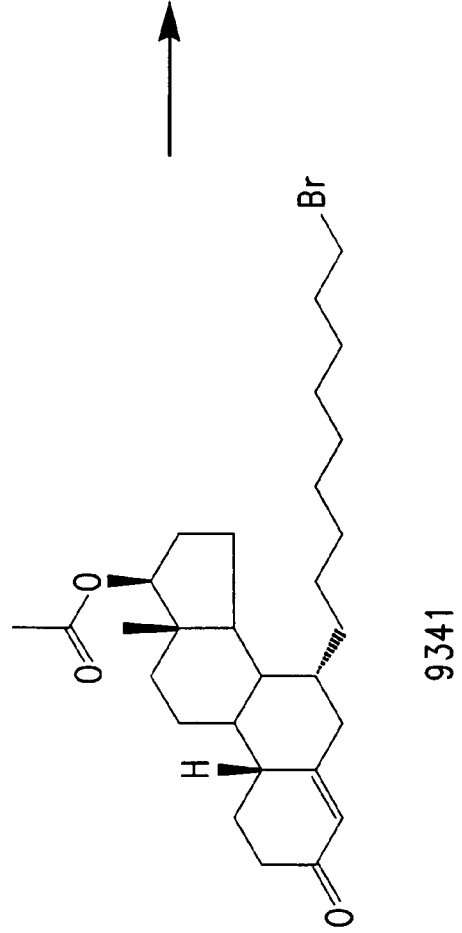

Preparation of Cp 9342 by Aromatization of Cp 9341 (Depicted in FIG. 6)

37 grams of Cp 9341 and 6.15 grams of lithium bromide are dissolved in 629 grams of acetonitrile and 18.5 grams of copper (II) bromide added. The mixture was stirred at ambient temperature for 7 hours, and then diluted with a solution of 74 grams of ammonium chloride in 942 grams of water. The mixture is further diluted with 37 grams of ammonium hydroxide solution 25% and 185 grams of ethyl acetate and left overnight under agitation in an open flask. The phases are separated and the upper (organic) phase is evaporated to an oily residue, which is dissolved in 500 grams of dichloromethane and washed with 370 grams of water. The phases are separated and the lower (organic) phase is evaporated to an oily residue. Weight of Cp 9342 obtained: 36.5 g Example 10

Figure 7:
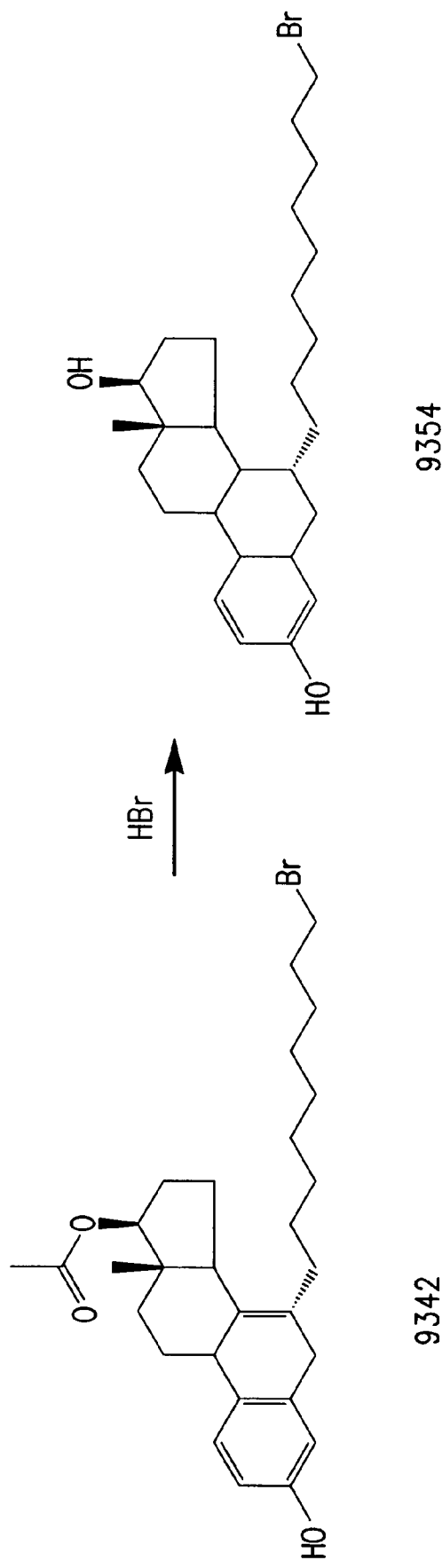
FIG. 7 is a schematic showing a method for making an intermediate, useful in the preparation of fulvestrant, according to the method of the invention.

Preparation of Cp 9354 from Cp 9342 (Depicted in FIG. 7)

To 61.7 grams of Cp 9342 in 494 grams of methanol was added 123.4 grams of hydrobromic acid 48% and the mixture was heated at 60° C. for 0.8 hours. The mixture was slowly cooled to 5° C. and seeded with a crystal of Cp 9354. After 1 hour the suspension was filtered and the crystals rinsed with a cold mixture of 100 grams methanol and 30 grams of water. After drying under vacuum at 60° C. to constant weight, 46 grams of Cp 9354 were obtained.

Example 11

Preparation of Cp 9360

A solution of 70.5 grams of 4,4,5,5,5-pentafluoropentane-1-ol in 1330 grams of dichloromethane was cooled under nitrogen and diluted with 59 grams of triethylamine followed by 54.5 grams of methanesulfonyl chloride. The solution was kept at 20° C. for 2 hours and then diluted with 1000 grams of water and agitated overnight. Evaporation of the organic phase afforded 109 grams of Cp 9360.

Example 12

Figure 10:
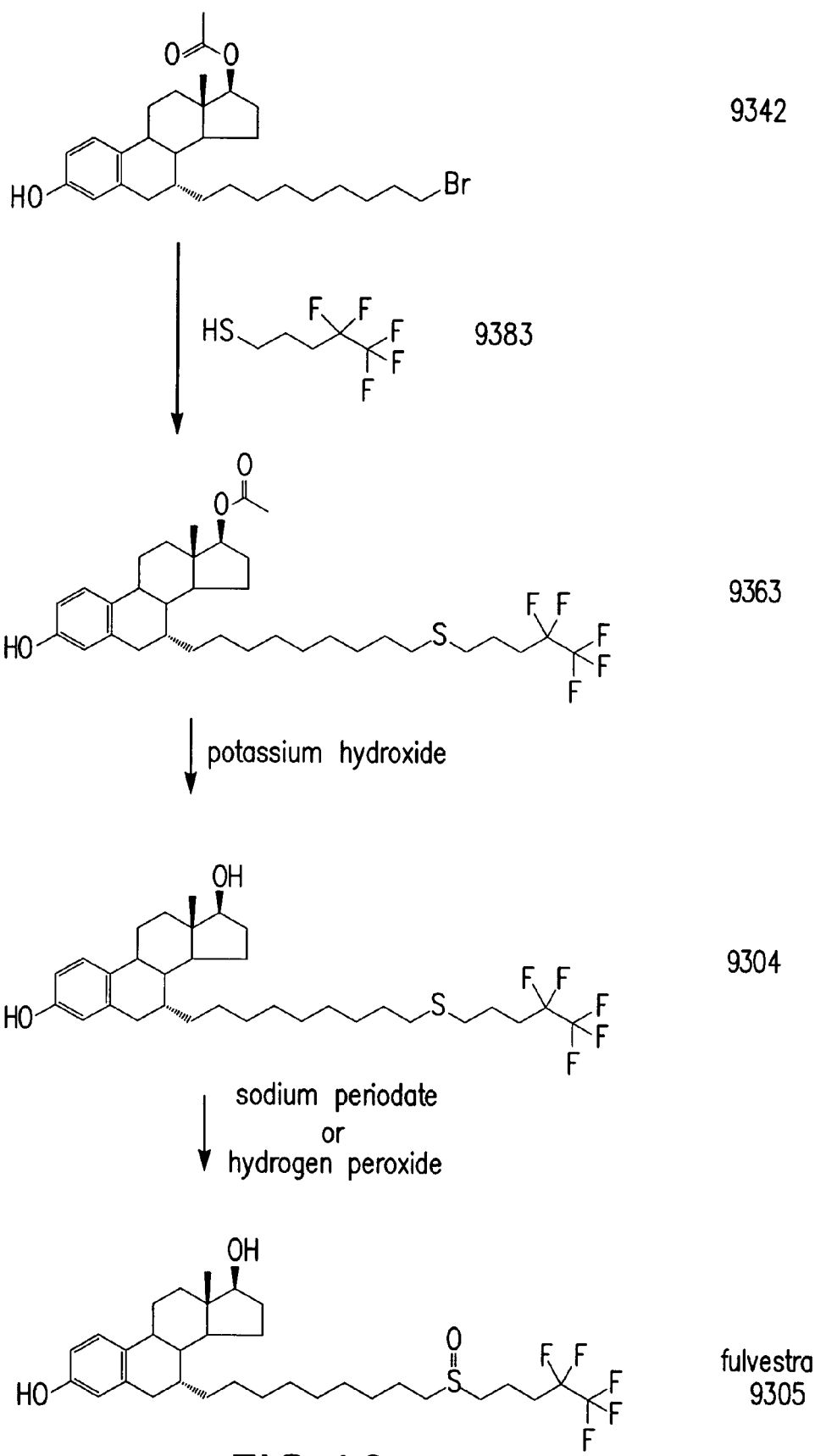
FIG. 10 is a schematic showing a method for making fulvestrant according to the method of the invention.

Preparation of Cp 9304 from Cp 9342 via Cp 9361, Cp 9362 and Cp 9363 (Depicted in FIG. 8 and Part of FIG. 10)

29 grams of Cp 9342 are heated at 80° C. for 16 hours in 198 grams of toluene and 99 grams of isopropanol with 5.3 grams (1.25 equivalents) of thiourea. The reaction mixture is evaporated under vacuum to an oily residue which is Cp 9361 that is diluted with 250 grams of dimethylacetamide, followed by combining with 13.7 g of Cp 9360 (prepared in example 11) and treating at room temperature for 1 hour with 22.3 grams of sodium hydroxide solution 50% to give Cp 9363. Hydrolysis of the 17-acetate group is this carried out by treatment at room temperature for 1 hour with a solution of 5 grams of potassium hydroxide in 45 grams of methanol. The reaction mixture is diluted with water and extracted with a mixture of toluene and ethyl acetate (1:1). Evaporation of the extracts afforded 36 grams of crude Cp 9304.

The crude product was purified by chromatography on silica gel (290 grams) eluting with toluene/ethyl acetate (95:5) to give 21 grams of pure Cp 9304.

Example 13

Preparation of Cp 9304 from Cp 9342 (Depicted in FIG. 10)

40 grams of Cp 9360 (prepared according to Example 11) were heated at 80° C. for 16 hours with 14.8 grams of thiourea and 345 grams of dimethylacetamide to give 400 grams of a 10% solution of Cp 9383.

To 90.7 grams of the 10% solution of Cp 9383 was added a solution of 18.5 grams of Cp 9342 in 76 grams of dimethylacetamide and the mixture was cooled to room temperature and treated with 9 grams of sodium hydroxide solution 50% for 0.6 hours. After neutralisation with 15 grams of acetic acid, the reaction mixture was then poured into water and extracted with toluene. Evaporation of the organic phase afforded 30 grams of Cp 9363.

30 grams of Cp 9363 were dissolved in 185 grams of methanol under nitrogen and the solution treated for 4 hours at room temperature with a solution of 9.25 grams of potassium hydroxide in methanol. After neutralization with 13.9 grams of acetic acid the mixture was evaporated under vacuum, then dissolved in dichloromethane, extracted with water and evaporated to provide crude Cp 9304.

The crude product is purified by chromatography on silica gel eluting with toluene/ethyl acetate (95:5) to provide purified Cp 9304.

Example 14

Figure 9:
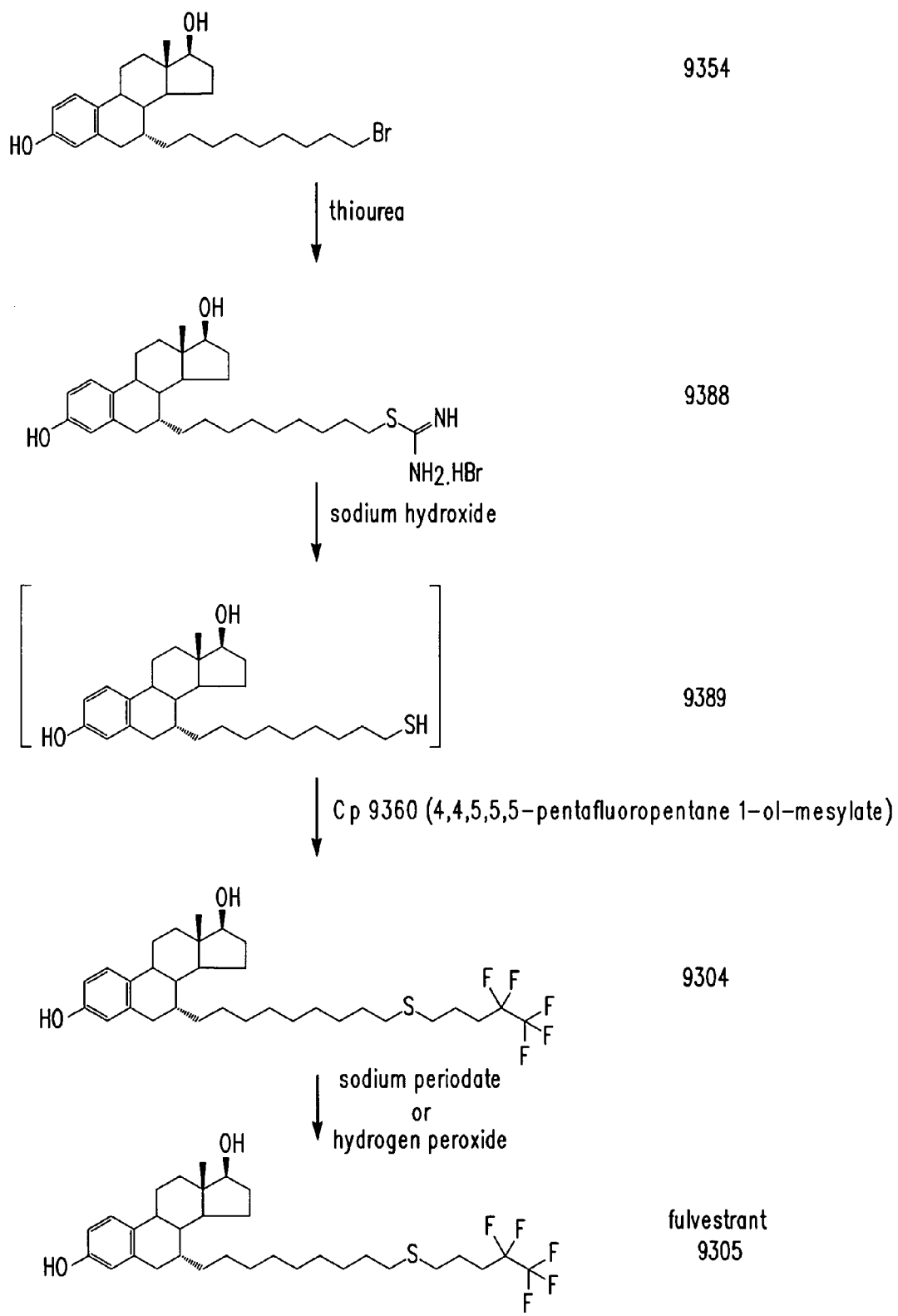
FIG. 9 is a schematic showing a method for making fulvestrant according to the method of the invention.

Preparation of Cp 9304 from Cp 9354—Indirect Process (Depicted in FIG. 9)

A mixture of 10 grams of Cp 9354 and 1.91 grams of thiourea in 100 grams of dimethylacetamide (to give Cp 9388) was heated at 80° C. for 16 hours, cooled to 20/25° C. and treated with 5.3 grams of Cp 9360 (prepared as in example 10) followed by 5.05 grams of sodium hydroxide solution 50%. After 1 hour the reaction mixture was neutralised with 7.5 grams of acetic acid, diluted with water, and extracted with toluene/ethyl acetate (1:1). Evaporation of the organic phase under vacuum gave an oily residue of Cp 9304.

The crude product is purified by chromatography on silica gel eluting with toluene/ethyl acetate (95:5) to provide purified Cp 9304.

Example 15

Figure 11:
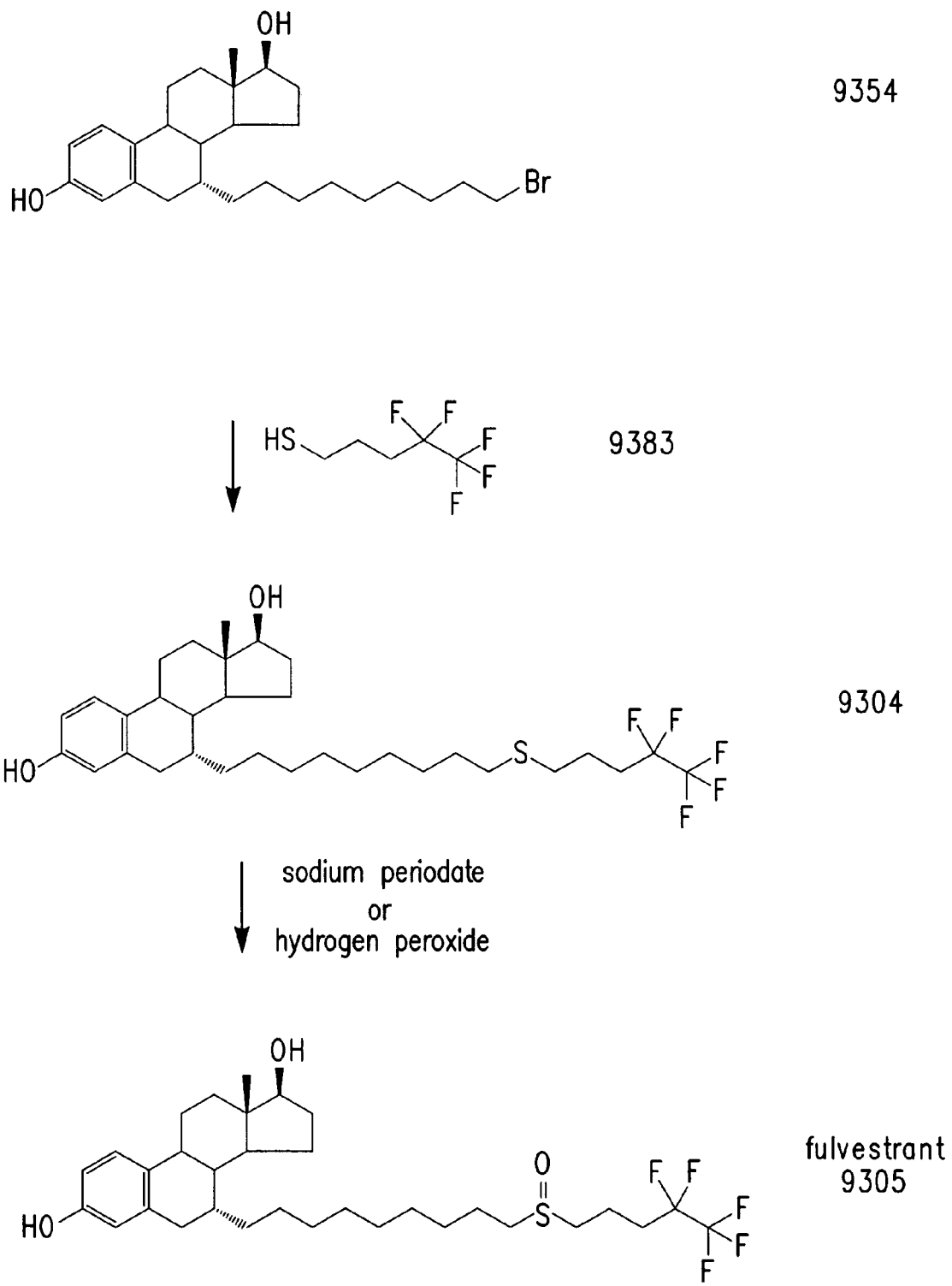
FIG. 11 is a schematic showing a method for making fulvestrant according to the method of the invention.

Preparation of Cp 9304 from Cp 9354—Direct Process (Depicted in FIG. 11)

To a solution of 20.5 grams of Cp 9354 in 100 grams of dimethylacetamide was added 109 grams of a 10% solution of Cp 9383 (prepared from Cp 9382 from example 10), followed by 10.3 grams of sodium hydroxide solution 50%. After 1 hour the reaction mixture was neutralised with 15 grams of acetic acid, diluted with water, and extracted with toluene/ethyl acetate (1:1). Evaporation of the organic phase under vacuum gave 30 grams of Cp 9304. The crude product was purified by chromatography on silica gel (250 grams) eluting with toluene/ethyl acetate (95:5) to give 25.3 grams of pure Cp 9304.

Example 16

Figure 12:
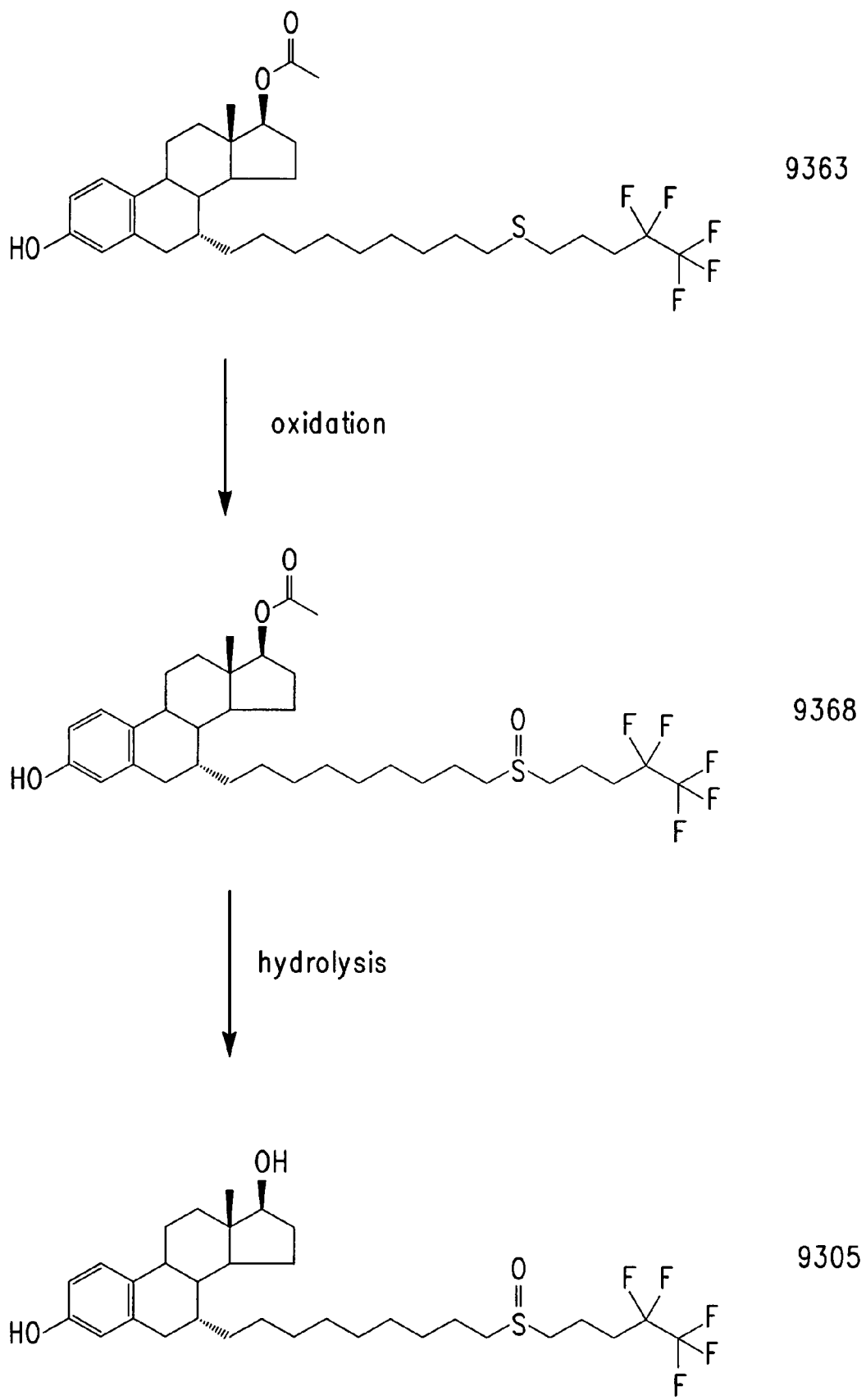
FIG. 12 is a schematic showing a method for making fulvestrant according to the method of the invention.

Preparation of Fulvestrant (Cp 9305) from Cp 9363—Indirect Process (Depicted in FIG. 12)

A solution of 40.5 grams of Cp 9363 in 320 grams tetrahydrofuran and 81 grams methanol was cooled to 5° C. and treated with a warm solution of 27 grams sodium (meta) periodate in 183 grams water. The mixture was allowed to stand at room temperature overnight, concentrated under vacuum and then dissolved in dichloromethane, extracted with water and evaporated to give 40 grams of Cp 9368 (fulvestrant 17-acetate).

The oily residue of Cp 9368 (40 grams) was dissolved in 320 grams of methanol under nitrogen and treated for 3 hours at room temperature with a solution of 20 grams of potassium hydroxide in 128 grams methanol. After neutralisation with 30 grams of acetic acid, the reaction mixture was concentrated under vacuum and then dissolved in dichloromethane, extracted with water and evaporated. The oily residue was crystallised from 400 grams of toluene, then dried under vacuum to constant weight. 26.6 grams of fulvestrant were obtained.

Example 17

Preparation of Fulvestrant (CP 9305) from Cp 9304—Direct Process (Depicted in FIG. 9)

A solution of 41 grams of Cp 9304 in 328 grams tetrahydrofuran and 82 grams methanol was cooled to 5° C. and treated with a warm solution of 27 grams sodium (meta) periodate in 185 grams water. The mixture was allowed to stand at room temperature overnight, concentrated under vacuum and then dissolved in dichloromethane, extracted with water, evaporated, and crystallised from toluene to give 28 grams of Cp 9305 (fulvestrant). Further purification can be effected by recrystallisation from ethyl acetate.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

We claim:

1. A compound of formula (I):

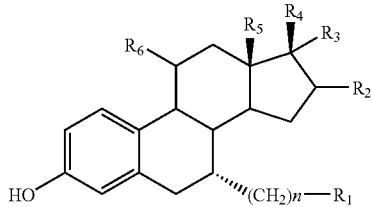

wherein n is 9; $R_1$ is Br; $R_2$, $R_3$, and $R_6$ are hydrogens; $R_4$ is hydroxy and $R_5$ is methyl.

2. A process for preparing the compound of formula (I) as claimed in claim 1, comprising combining the compound of formula (VI)

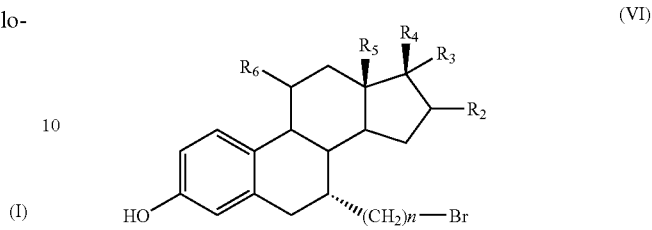

wherein n and $R_2$, $R_3$, $R_5$ and $R_6$ are as defined in claim 1 and $R_4$ is a $C_{1-6}$ acyloxy, with a $C_{1-6}$ alcohol and mineral acid, at a temperature of about 50° C. to about 70° C.

3. The process of claim 2, wherein the mineral acid is HBr.

4. The process of claim 2 or claim 3, wherein the temperature is about 60° C.

5. The process of claim 2, further comprising converting the obtained product to fulvestrant.

* * * * *